US011992560B2

(12) United States Patent
Calza et al.

(10) Patent No.: US 11,992,560 B2
(45) Date of Patent: May 28, 2024

(54) ELECTROSPUN FIBERS FOR A LOCAL RELEASE OF AN ANTI-INFLAMMATORY DRUG AND A PROMYELINATING DRUG

(71) Applicant: ALMA MATER STUDIORUM—UNIVERSITÀ DI BOLOGNA, Bologna (IT)

(72) Inventors: Laura Calza, Monterenzio (IT); Luciana Giardino, Monterenzio (IT); Maria Letizia Focarete, Bologna (IT); Chiara Gualandi, Molinella (IT); Maria-Laura Bolognesi, Bologna (IT); Nadia Passerini, Bologna (IT); Giampiero Pagliuca, Bologna (IT); Teresa Gazzotti, Bologna (IT); Elisa Zironi, Sasso Marconi (IT)

(73) Assignee: ALMA MATER STUDIORUM—UNIVERSITÀ DI BOLOGNA, Bologna (IT)

( * ) Notice: Subject to any disclaimer, the term of this patent is extended or adjusted under 35 U.S.C. 154(b) by 0 days.

(21) Appl. No.: 17/251,601

(22) PCT Filed: Jun. 14, 2018

(86) PCT No.: PCT/IT2018/000084
§ 371 (c)(1),
(2) Date: Dec. 11, 2020

(87) PCT Pub. No.: WO2019/239436
PCT Pub. Date: Dec. 19, 2019

(65) Prior Publication Data
US 2021/0244677 A1 Aug. 12, 2021

(51) Int. Cl.
*A61K 9/70* (2006.01)
*A61K 9/00* (2006.01)
(Continued)

(52) U.S. Cl.
CPC .............. *A61K 9/70* (2013.01); *A61K 9/0024* (2013.01); *A61K 31/12* (2013.01); *A61K 31/19* (2013.01);
(Continued)

(58) Field of Classification Search
CPC .... A61K 31/40; A61K 31/197; A61K 31/192; A61K 31/198; A61K 31/19; A61K 9/70;
(Continued)

(56) References Cited

U.S. PATENT DOCUMENTS 9,498,536 B2    11/2016   Mousa et al.
2003/0185872 A1*   10/2003   Kochinke ................. A61F 2/02
                                                                                                     424/426
(Continued)

FOREIGN PATENT DOCUMENTS

WO   WO-2004014304 A2   2/2004
WO   WO-2012065175 A2   5/2012
(Continued)

OTHER PUBLICATIONS

Hawkins, K.P., et al., "Probabilistic human action prediction and wait-sensitive planning for responsive human-robot collaboration," *2013 13th IEEE-RAS International Conference on Humanoid Robots (Humanoids)*—Atlanta, GA, United States (Oct. 15-17, 2013), pp. 499-506, Institute of Electrical and Electronics Engineers, United States (2013).
(Continued)

*Primary Examiner* — Jianfeng Song
(74) *Attorney, Agent, or Firm* — Sterne, Kessler, Goldstein & Fox P.L.L.C.

(57) ABSTRACT

The present invention relates to electro spun fibers for a local release in the central nervous system of an anti-inflammatory and a promyelinating agent over a defined time-window, in order to limit secondary neurodegeneration triggered
(Continued)

by the glutamate release and supported by on-going inflammation. The combined treatment aimed to reduce inflammation and improve remyelination in the very early stage of the pathology improving the chronic clinical outcome of the lesion. In particular the present invention relates to electrospun polymeric fibers, wherein said fibers are loaded with 3,3,5-Triiodo-L-thyronine (T3) and Ibuprofen.

11 Claims, 14 Drawing Sheets

(51) Int. Cl.
| | |
|---|---|
| *A61K 31/12* | (2006.01) |
| *A61K 31/19* | (2006.01) |
| *A61K 31/192* | (2006.01) |
| *A61K 31/196* | (2006.01) |
| *A61K 31/197* | (2006.01) |
| *A61K 31/198* | (2006.01) |
| *A61K 31/40* | (2006.01) |
| *A61K 31/405* | (2006.01) |
| *A61K 31/407* | (2006.01) |
| *A61K 31/42* | (2006.01) |
| *A61K 31/421* | (2006.01) |
| *A61K 31/4418* | (2006.01) |
| *A61K 31/5415* | (2006.01) |
| *A61K 31/5575* | (2006.01) |
| *A61K 31/603* | (2006.01) |
| *A61K 31/704* | (2006.01) |
| *A61P 25/28* | (2006.01) |

(52) U.S. Cl.
CPC .......... *A61K 31/192* (2013.01); *A61K 31/196* (2013.01); *A61K 31/197* (2013.01); *A61K 31/198* (2013.01); *A61K 31/40* (2013.01); *A61K 31/405* (2013.01); *A61K 31/407* (2013.01); *A61K 31/42* (2013.01); *A61K 31/421* (2013.01); *A61K 31/4418* (2013.01); *A61K 31/5415* (2013.01); *A61K 31/5575* (2013.01); *A61K 31/603* (2013.01); *A61K 31/704* (2013.01); *A61P 25/28* (2018.01)

(58) Field of Classification Search
CPC .... A61K 31/12; A61K 31/405; A61K 31/603; A61K 31/4418; A61K 31/704; A61K 31/407; A61K 31/421; A61K 31/196; A61K 31/5415; A61K 31/42; A61K 31/5575; A61K 9/0024; A61P 25/28
See application file for complete search history.

(56) References Cited

U.S. PATENT DOCUMENTS

| | | | |
|---|---|---|---|
| 2004/0156904 A1 | 8/2004 | Saltman et al. | |
| 2006/0013869 A1* | 1/2006 | Ignatious | D01F 1/10 424/464 |
| 2012/0004199 A1 | 1/2012 | McNeil et al. | |
| 2013/0030340 A1* | 1/2013 | Vincent | D04H 1/43828 442/164 |
| 2014/0294931 A1 | 10/2014 | Mousa et al. | |
| 2015/0335451 A1* | 11/2015 | Liu | B29C 48/05 623/1.46 |
| 2016/0287242 A1* | 10/2016 | Troxel | A61L 31/045 |
| 2016/0331875 A1* | 11/2016 | Grinstaff | A61L 27/50 |
| 2017/0304214 A1 | 10/2017 | Hoke et al. | |
| 2018/0296489 A1* | 10/2018 | Louw | A61K 36/53 |

FOREIGN PATENT DOCUMENTS

| | | |
|---|---|---|
| WO | WO-2019234700 A1 | 12/2019 |
| WO | WO-2019239436 A1 | 12/2019 |

OTHER PUBLICATIONS

International Search Report and Written Opinion for International Application No. PCT/IB2019/054763, European Patent Office, Netherlands, dated Oct. 8, 2019, 17 pages.

Zanchettin, A.M., et al., "Probabilistic inference of human arm reaching target for effective human-robot collaboration," *2017 IEEE/RSJ International Conference on Intelligent Robots and Systems (IROS)*—Vancouver, BC, Canada (Sep. 24-28, 2017), pp. 6595-6600, Institute of Electrical and Electronics Engineers, United States (2017).

Baek, H.H., et al., "Development of novel ibuprofen-loaded solid dispersion with enhanced bioavailability using cycloamylose," *Arch Pharm Res* 35(4):683-689, Pharmaceutical Society of Korea, South Korea (2012).

Basso, D.M., et al., "MASCIS evaluation of open field locomotor scores: effects of experience and teamwork on reliability," *Journal of Neurotrauma* 13(7):343-359, Mary Ann Liebert Inc., United States (1996).

Basso, D.M., et al., "Basso Mouse Scale for locomotion detects differences in recovery after spinal cord injury in five common mouse strains," *Journal of Neurotrauma* 23(5):635-659, Mary Ann Liebert Inc., United States (2006).

Chiodi, V., et al., "Unbalance of CB1 receptors expressed in GABAergic and glutamatergic neurons in a transgenic mouse model of Huntington's disease," *Neurobiol Dis* 45(3):983-91, Academic Press Inc., United States (2012).

Dell'Acqua, M.L., et al., "Functional and molecular evidence of myelin- and neuroprotection by thyroid hormone administration in experimental allergic encephalomyelitis," *Neuropathol Appl Neurobiol* 38(5):454-70, Wiley-Blackwell Publishing Ltd., United Kingdom (2012).

D'Intino, G., et al., "Triiodothyronine administration ameliorates the demyelination/remyelination ratio in a non-human primate model of multiple sclerosis by correcting tissue hypothyroidism," *J Neuroendocrinol* 23(9):778-90, Wiley-Blackwell Publishing Ltd., United Kingdom (2011).

Fernández, M., et al., "Inflammation severely alters thyroid hormone signaling in the central nervous system during experimental allergic encephalomyelitis in rat: Direct impact on OPCs differentiation failure," *Glia* 64(9):1573-1589, John Wiley and Sons Inc., United States (2016).

Fernández-Carballido, A., et al., "Biodegradable ibuprofen-loaded PLGA microspheres for intraarticular administration. Effect of Labrafil addition on release in vitro," *International Journal of Pharmaceutics* 279(1-2):33-41, Elsevier, Netherlands (2004).

Gryczke, A., et al., "Development and evaluation of orally disintegrating tablets (ODTs) containing Ibuprofen granules prepared by hot melt extrusion," *Colloids and Surfaces B: Biointerfaces* 86(2):275-284, Elsevier, Netherlands (2011).

International Conference on Harmonisation (ICH), "Guidance for Industry: Q2B Validation of Analytical Procedures: Methodology," Food and Drug Administration, U.S. Department of Health & Human Services, 13 pages.

International Search Report and Written Opinion International Application No. PCT/IT2018/000084, European Patent Office, Netherlands, dated Feb. 19, 2019, 11 pages.

Kenawy, E.R., et al., "Processing of polymer nanofibers through electrospinning as drug delivery systems," *Materials Chemistry and Physics* 113(1):296-302, Elsevier BV, Netherlands (2009).

Kiebooms, J.A.L., et al., "Validated ultra high performance liquid chromatography-tandem mass spectrometry method for quantitative analysis of total and free thyroid hormones in bovine serum," *Journal of Chromatography A* 1345:164-73, Elsevier, Netherlands (2014).

(56) References Cited

OTHER PUBLICATIONS

Park, J.Y., and Lee, I.H., "Controlled release of ketoprofen from electrospun porous polylactic acid (PLA) nanofibers," *Journal of Polymer Research 18*(6):1287-1291, Springer, Netherlands (2010).

Pires, L.R., et al., "Ibuprofen-loaded fibrous patches-taming inhibition at the spinal cord injury site," *Journal of Materials Science: Materials in Medicine 28*(10):157, Springer New York LLC, United States (2017).

Ramsey, J.B.G., et al., "Care of rats with complete high-thoracic spinal cord injury," *J Neurotrauma 27*(9):1709-22, Mary Ann Liebert Inc., United States (2010).

Shultz, R.B., et al., "Local delivery of thyroid hormone enhances oligodendrogenesis and myelination after spinal cord injury," *J Neural Eng 14*(3):036014, IOP Publishing Ltd., United Kingdom (2017).

Sütő, B., et al., "Development of ibuprofen-loaded nanostructured lipid carrier-based gels: characterization and investigation of in vitro and in vivo penetration through the skin," *International Journal of Nanomedicine 11*:1201-1212, Dove Medical Press Ltd., New Zealand (2016).

United States Pharmacopeia—National Formulary, "Chapter 621: Chromatography" from First Supplement to USP 40—NF 35, accessed at https://www.bioglobax.com/wp-content/uploads/2018/08/621-Chromatography.pdf on Dec. 1, 2020, 12 pages.

Yu, D.G., et al., "Oral fast-dissolving drug delivery membranes prepared from electrospun polyvinylpyrrolidone ultrafine fibers," *Nanotechnology 20*(5):055104, IOP Publishing Ltd., United Kingdom (2009).

Zhu, Y., et al., "Electrospun fibers of poly(l-lactic acid) containing lovastatin with potential applications in drug delivery," *Journal of Applied Polymer Science 134*(36):45287, John Wiley and Sons Inc., United States (2017).

\* cited by examiner

ELECTROSPUN FIBERS FOR A LOCAL RELEASE OF AN ANTI-INFLAMMATORY DRUG AND A PROMYELINATING DRUG The present invention relates to electrospun fibers for a local release of an anti-inflammatory and a promyelinating agent over a defined time-window, in order to limit secondary neurodegeneration triggered by the glutamate release and supported by on-going inflammation in the nervous system. The combined treatment aimed to reduce inflammation and improve remyelination in the very early stage of the pathology improving the chronic clinical outcome of the lesion. In particular the present invention relates to electrospun polymeric fibers, wherein said fibers are loaded with a promyelinating agent, such as 3,3,5-Triiodo-L-thyronine (T3) and an anti-inflammatory agent, such as Ibuprofen.

STATE OF THE PRIOR ART

Spinal cord injury represents a global level of causes of death and disability. The incidence reported in the literature varies from 15 to 45 cases per million. The outcomes are influenced by the surgical and pharmacological treatment during the acute phase, the place where medical care is provided, the length of hospital stay and the availability of services involved. The cost analysis shows a high correlation with the level of health and with the completeness of the lesion measured according to the ASIA scale (American Spinal Injury Association). At the current state, the pharmacological interventions are still limited and the routine protocols are aimed at reducing oedema, although the routine use of steroids in patients with spinal cord injuries has been largely abandoned and considered a 'harmful standard of care'. Some drugs, approved for other neurogenic diseases are currently being tested (eg Riluzole, erythropoietin, Nogo-A targeting, Rho inhibitor Cethrin and minocycline). However, no one at the present showed evidences of I have a couple questions (of course)1 auspicious efficacy in the recovery of the sensorial-motor function". It is therefore a great step forward in neurobiology to clinical SCI experimentation, to develop therapeutic strategies in relation to specific biological targets, focusing on early events in SCI.

The current pharmacological failure may be at least for two reasons: (i) Drugs are used in monotherapy and as such are inadequate to break the vicious cycle between increased inflammation and decrease remyelination subsequent to the lesion. Accumulating evidence indicate that the multifaceted inhibitory nature of SCI requires a multi-target (combinatorial) therapeutic approach. (ii) The currently available drugs, including NSAID and cortisones, suffer from severe systemic side-effects, in particular for dosages and treatment duration suitable to appropriately target the spinal cord.

A recent study deals with the development of a novel hydrogel-based drug delivery system for local delivery of T3 to the spinal cord injury site (Shultz, et al. 2017). Authors demonstrated that T3 can be delivered at doses comparable to safe human doses by accurately regulating initial drug loading and gel volume. However, in vitro tests showed that an initial burst T3 release much higher than the safe dose was unavoidable and a pre-implantation treatment in vitro was suggested to eliminate the burst in vivo. The burst release is a common phenomenon in drug delivery systems that is even further sharpened when using highly hydrophilic matrices like hydrogels.

The U.S. Pat. No. 9,498,536 discloses nanoparticles for management inflammatory conditions in a subject with a cancer, wherein said nanoparticles consisting of a biopolymer covalently linked to tri-iodothyroacetic or tetra-iodothyroacetic acid and other thyroid partial agonists or antagonists, alone or in combination with a second agent, such as non-steroidal anti-inflammatory drugs.

The aim of this invention is to provide new and more effective scaffold for targeting inflammation and demyelination in the very early stage of SCI lesion, e.g. to prevent/limit the secondary phase, that occurs within the time-window for surgical spine stabilization (when necessary), being this a treatment-orphan phase of the neuropathology.

SUMMARY OF THE INVENTION

The inventors generate electrospun fibers for a local release of an anti-inflammatory and a promyelinating agent over a defined time-window, in order to limit secondary neurodegeneration triggered by the glutamate release and supported by on-going inflammation. The combined treatment aimed to reduce inflammation and improve remyelination in the very early stage of the pathology improving the chronic clinical outcome of the lesion.

The present invention provides a multi-drug local delivery system allowing the simultaneous administration of a NSAID (ibuprofen) and a remyelinating agent (T3, a natural hormone), over an estimated time of 8 to 14 days, to be implanted directly on top of the lesion for example within 24 hours after traumatic spinal cord injury. The experimental data reported in details in the examples show the effectiveness of the functionalized electrospun fibers generated by the inventors and their advantages.

Moreover, loading the drug into the electrospun fibers represents an effective way to protect the drug from the outer environment and to better control the release kinetics. The loading into the fibers can be performed by dispersing the drug in the polymeric matrix through a direct blending approach or by loading the drug in a core/shell fiber structure.

Accordingly, a first object of the invention is electrospun polymeric fibers, wherein part or all of said fibers are loaded with a promyelinating agent, in particular the hormone T3 and another part or all of said fibers are loaded with an anti-inflammatory agent, in particular Ibuprofen.

A further object of the invention is electrospun polymeric fibers for use in the treatment of a spinal cord injury, particular in the prevention and/or the treatment of the secondary neurodegeneration in a subject with a spinal cord injury.

A further object of the invention is an implantable scaffold comprising or consisting of said electrospun fibers.

A further object of the invention is a process for manufacturing said electrospun fibers comprising a step of electrospinning a polymeric solution comprising a promyelinating agent, in particular the hormone T3 and an anti-inflammatory agent, in particular Ibuprofen.

A further object of the invention is a composition comprising a mixture of polymeric fibers, wherein part or all of said fibers are loaded with a promyelinating agent, in particular the hormone T3 and another part or all of said fibers are loaded with an anti-inflammatory agent, in particular Ibuprofen and a diluent and/or an excipient and/or a carrier.

DETAILED DESCRIPTION OF THE INVENTION

Figure 1:
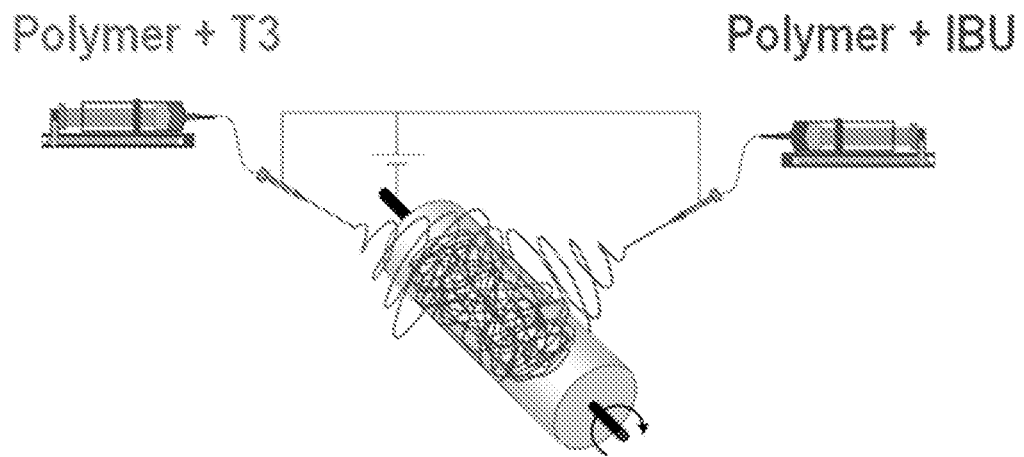
FIG. 1 shows a schematic representation of the process for manufacturing the electrospun polymeric fibers according to one embodiment of the invention.

As previously indicated, the present invention relates to electrospun polymeric fibers, wherein said fibers are loaded with a promyelinating and an anti-inflammatory agent. In particular it relates to electrospun polymeric fibers wherein part or all of said fibers are loaded with a promyelinating agent and another part or all of said fibers are loaded with an anti-inflammatory agent.

In the present description, the expression "promyelinating agent" means any agent that promote the differentiation of the meylinating cells, e.g. oligodendrocyte precursor cells, into myelinating cells, e.g. mature, myelinating oligodendrocytes.

In the present description, the expression "loaded with a promyelinating agent or an anti-inflammatory agent" means that the agent/drug/active ingredients are mixed with the polymeric solution and then the obtained mixture is electrospun; in this way, the agent/drug/active ingredient is encapsulated inside the electrospun fibers in a non-covalent manner.

According to one embodiment said promyelinating agent is selected from a thyroid hormone receptor agonist, preferably a thyroid hormone receptor agonist selected from 3,3,5-Triiodo-L-thyronine (T3), L-thyroxine (T4), DITPA (3,5-Diiodothyropropionic acid), DIMIT (3,5-dimethyl-3-isopropyl-L-thyronine), DIBIT (3,5-Dibromo-3'-isopropyl-L-thyronine), MIBRT (3,5-dibromo-4-(3'isopropyl-4'-hydroxyphenoxy)benzoic acid), Eprotirome, Sobetirome, MGL-3196 (2-[3,5-dichloro-4-[(6-oxo-5-propan-2-yl-1H-pyridazin-3-yl)oxy]phenyl]-3,5-dioxo-1,2,4-triazine-6-carbonitrile).

According to one embodiment said anti-inflammatory agent is selected from a non-steroidal anti-inflammatory drug (NSAID), a salicylate, an anti-inflammatory glucocorticoid, and pirfenidone.

According to one embodiment said anti-inflammatory agent is a non-steroidal anti-inflammatory drug (NSAID) selected from ibuprofen, flurbiprofen, diclofenac, and diclofenac with misoprostol, indomethacin, ketoprofen, fenbrufen, naproxen, sulindac, celecoxib, nabumetone, mefenamic acid, oxyphenbutazone, diflunisal, etodolac, fenoprofen, flurbiprofen, meclofenamate, meloxicam, nabumetone, oxaprozin, piroxicam, tolmetin, valdecoxib and propionic acid derivatives or their mixture.

According to one embodiment said anti-inflammatory agent said promyelinating agent is 3,3,5-Triiodo-L-thyronine (T3) and said anti-inflammatory agent is ibuprofen.

According to one embodiment said polymeric fibers are biocompatible polymeric fibers, preferably selected from synthetic polyesters (e.g. polylactic acid (PLLA), polyglycolic acid (PGA), polycaprolactone (PCL) and/or their copolymers such as poly(lactic-co-glycolic acid) (PLGA), and/or their mixtures), polyurethanes, polyamides, fluorinate polymers, or their copolymers and/or mixture, or natural polymers preferably selected from proteins, polysaccharides, polyesters, polypeptides and their copolymers and/or their mixtures.

According to one embodiment between 10 and 90%, preferably between 20 and 50%, of said fibers are loaded with the promyelinating agent and/or between 10 and 90%, preferably between 20 and 50% of said fibers are loaded with the anti-inflammatory agent.

According to one embodiment all the electrospun fibers are loaded with both active agents, i.e. the promyelinating agent and the anti-inflammatory agent. According to one embodiment said fibers have a diameter between 50 and 5000 nm.

According to one embodiment the amount of the anti-inflammatory agent in said fibers is PLLA, 20% w/v dissolved in DCM:DMF 70:30 (v/v), with the addition of 5% w/w or 10% w/w of IBU, while the amount of said promyelinating agent is—

PLLA, 20% w/v dissolved in DCM:MetOH 70:30 (v/v), with the addition of 0.6% w/w of T3.

The electrospun fibers herein disclosed may be used as or in an implantable scaffold in a method for surgery in a subject with a spinal cord injury.

It's also an object of the present invention a process for manufacturing the electrospun fibers according to any one of the embodiments herein disclosed comprising a step of electrospinning a polymeric solution comprising a promyelinating agent and an anti-inflammatory agent.

According to one embodiment the process comprising the steps of:
a) preparing a polymeric solution comprising a promyelinating agent:
b) preparing a polymeric solution comprising an anti-inflammatory agent:
c) electrospinning the solutions prepared in the step a) and/or b).

According to one embodiment the voltage used in the electrospinning steps of the process is between 15 and 20 kV and/or a flow rate between 0.5 and 2.5 ml/h.

According to one embodiment of the process the blend solution comprises a promyelinating agent in a concentration between 0.1 and 2% weight/weight (w/w) and/or the anti-inflammatory agent in a concentration between 1 and 10% w/.

According to one embodiment in the blending process the promyelinating and/or the anti-inflammatory agents and a biopolymer selected preferably selected from synthetic polyesters (e.g. polylactic acid (PLLA), polyglycolic acid (PGA), polycaprolactone (PCL) and/or their copolymers such as poly(lactic-co-glycolic acid) (PLGA), and/or their mixtures), polyurethanes, polyamides, fluorinate polymers, or their copolymers and/or mixture, or natural polymers preferably selected from proteins, polysaccharides, polyesters, polypeptides and their copolymers and/or their mixtures, are mixed with an organic solvent selected from Dimethylformamide (DMF), dimethyl carbonate (DMC), Methanol (MetOH) or their mixture. The prepared blends are then subjected to electrospinning, preferably the blend with the anti-inflammatory agent and the blend with the promyelinating agent are prepared and subjected to electrospinning separately (e.g. FIG. 1).

Examples aimed at illustrating some embodiments of the present invention are reported here below; in no way, such examples are to be construed as a limitation of the present description and of the subsequent claims.

EXAMPLES AND EXPERIMENTAL DATA

Example 1 (Material Fabrication)

PLGA 50:50 (RESOMER® RG 504 H, inherent viscosity=0.45-0.60 dL/g), PLGA 75:25 (RESOMER® RG 756 S, inherent viscosity=0.71-1.0 dL/g), PLGA 85:15 (RESOMER® RG 858 S, inherent viscosity=1.3-1.7 dL/g), PLLA (RESOMER® L 206 S, inherent viscosity=0.8-1.2 dL/g) were purchased from Evonik Industries. N,N-Dimethylformamide (DMF), dichloromethane (DCM), Methanol (MeOH) were purchased from Sigma Aldrich. 3,3,5-Triiodo-L-thyronine sodium salt (T3) ≥95% (HPLC) was purchased from Sigma Aldrich. Ibuprofen was purchased from Sigma Aldrich.

For the preparation of the drug loaded fibers the following polymeric solutions were used:
PLGA 50:50, 15% w/v dissolved in DCM:DMF 70:30 (v/v) with the addition of 5% w/w of IBU;
PLGA 75:25, 20% w/v dissolved in DCM:DMF 70:30 (v/v) with the addition of 5% w/w of IBU;
PLGA 85:15, 8% w/v dissolved in DCM:DMF 70:30 (v/v), with the addition of 5% w/w of IBU;
PLLA, 20% w/v dissolved in DCM:DMF 70:30 (v/v), with the addition of 5% w/w or 10% w/w of IBU.
PLLA, 20% w/v dissolved in DCM:MetOH 70:30 (v/v), with the addition of 0.6% w/w of T3.

Similar polymeric solutions not containing the drugs were prepared as a reference. An electrospinning apparatus (Spinbow srl, Italy), comprised of a high-voltage power supply, a syringe pump, a stainless steel blunt-ended needle (inner diameter 0.84 mm) connected with the power supply electrode, and a grounded aluminum drum-type collector (diameter 5 cm) rotating at 75 rpm, was used (FIG. 1). Polymer solution was dispensed through a PTFE tube to the needle, which was placed vertically on the collecting drum at a distance of 20 cm. All scaffolds were produced by electrospinning the polymeric solution for a period of 2 h, to gain samples with thickness in the range 150-170 μm. The electrospun scaffolds were produced at RT and at relative humidity of 30%. The Table below reports the electrospinning parameters used to produce the drug-loaded scaffolds. The same experimental conditions were used to produce plain fibers.

| Polymer | Drug (w/w %) | Flow rate (ml/h) | Needle-to-collector distance (cm) | Voltage (kV) |
|---|---|---|---|---|
| PLGA 50:50 | IBU (5%) | 0.8 | 20 | 20 |
| PLGA 75:25 | IBU (5%) | 1.5 | 20 | 18 |
| PLGA 85:15 | IBU (5%) | 0.8 | 20 | 18 |
| PLLA nano | IBU (5%) | 1.2 | 20 | 18 |
| PLLA micro | IBU (5%) | 2.4 | 20 | 18 |
| PLLA nano | IBU (10%) | 1.2 | 20 | 18 |
| PLLA nano | T3 (0.6%) | 1.2 | 20 | 18 |

Example 2 (Analytical Procedures: Ibuprofen)

The aim was to develop a simple and rapid HPLC-UV method for the quantification of Ibuprofen (IBU) in different matrices: electrospun fibers and release media. The review of literature revealed that numerous HPLC methods have been developed for the determination of IBU (Colloids and Surfaces B: Biointerfaces 86 (2011) 275-284; International Journal of Pharmaceutics 279 (2004) 33-41; International Journal of Nanomedicine 2016:11 1201-1212; Arch Pharm Res Vol 35, No 4, 683-689, 2012). Therefore, the HPLC-UV method was developed by conveniently adapting these HPLC methods to our conditions.

The in vitro drug release studies aimed to correlate the physicochemical properties of the electrospun fibers with their performance in order:
(i) To optimize the design of the drug delivery systems by varying the polymer properties (lactide/glycolide ratio), the amount of drugs and the drug incorporation method (physical incorporation or polymer-drug conjugation).
(ii) To select the systems for the in vivo testing.

Material

Highly pure deionized water obtained from a Millipore Elix 10 water purification system was used to prepare all aqueous solutions. Ibuprofen (IBU) was purchased from Sigma Aldrich; $NH_4H_2PO_4$, $CH_3CN$ (ACN) and $(CH_3)_2SO$ (DMSO) was purchased from Sigma-Aldrich. All HPLC solvents were of analytical grade.

HPLC-UV Method Optimization

Ibuprofen was analyzed by HPLC system consisted of two mobile phase delivery pumps (LC-10ADvp, Shimadzu, Japan) and a UV-vis detector (SPD-10Avp, Shimadzu, Japan). An autosampler (SIL-20A, Shimadzu, Japan) was used to inject samples (20 μl) onto a Kinetex C18 (150 mm×4.60 mm×5 μm) column (Phenomenex, Bologna, Italy). The mobile phase consisted of $NH_4H_2PO_4$ (0.02 M with pH adjusted at 3.0 using ortho phosphoric acid) and $CH_3CN$ (43:57, V/V). The mobile phase was filtered through a 0.22-μm Sartorius filter before use. The flow rate was 1 ml/min and the detection wavelength was set at 220 nm. The retention time of IBU was 5.2 minutes.

The following method characteristics were addressed: linearity, range, limit of detection (LOD) and limit of quantitation (LOQ).

Preparation of Standard Solutions

A stock solution 10 mg/mL of IBU in ACN was prepared, than a series of solutions having concentrations between 0.05 and 20 μg/ml were obtained by dilution in a mobile phase ($ACN:NH_4H_2PO_4$ v/v).

Linearity and Range

Linearity was assessed by analyzing IBU at seven different concentrations within 0.05-20 μg/ml of the nominal standard concentration. The linearity of the proposed method was evaluated by using calibration curve to calculate coefficient of correlation, slope, and intercept values.

Limit of Detection (LOD) and Limit of Quantitation (LOQ)

LOD is the lowest amount of analyte in a sample that can be detected but not necessarily quantified. LOQ is the lowest amount of analyte in a sample that may be determined with acceptable accuracy and precision.

The values corresponding to LOD and LOQ were estimated as IBU concentrations that give rise to peaks whose heights correspond to 3 and 10 times the background noise.

Example 3 (Analytical Procedures: T3)

The Reagents and Chemicals

Standard Triiodothyronine (3,3,5-Triiodo-L-thyronine sodium salt (T3) ≥95% (HPLC) was purchased from Sigma Aldrich)

Methanol, acetonitrile and formic acid were of LC-MS grade and were purchased from Sigma Aldrich (St. Louis, MO, USA). Ultrapure water was produced in-house with a Human Power I system (Seoul, Korea). Oasis® HLB 200 mg SPE cartridges were purchased from Waters (Milford, MA, USA)

Sample Preparation

Sample clean-up was carried modifying a previously described procedure (J. A. L. Kiebooms, J. Wauters, J. Vanden Bussche, L. Vanhaecke. Journal of Chromatography A, 1345 (2014) 164-173)

Briefly, after conditioning the Oasis® HLB cartridge with 2 mL of methanol and 2 mL of water, always avoiding the solid phase to go dry, 1 mL of sample was loaded. Once all the solution had passed through the column, the washing was performed with 3 mL of a mixture of water/methanol (80/20, v/v), then vacuum was applied for 5 min to remove eventual residual drops. The analyte was eluted with 1 mL of methanol containing 0.1% of formic acid in vial prior to analysis in UPLC-MS/MS.

UPLC-MS/MS Analysis

Analysis were performed on an UPLC-MS/MS system, including a Waters Acquity UPLC® binary pump, equipped with built-in vacuum degasser, thermostated autosampler and column heater. Chromatographic separation was achieved using a Waters Acquity UPLC® BEH C18 reversed-phase column (50×2.1 mm, 1.7 μm), fitted with a Waters VanGuard guard column with the same packaging (Waters Corporation, Milford, MA, USA)

The mobile phase consisted of a mixture of water/methanol (90/10, v/v) containing 0.1% of formic acid (solvent A) and methanol containing 0.1% of formic acid (solvent B). The gradient (constant flow rate at 0.3 mL/min) started with 70% A and 30% B, then followed by a gradient of solvent B (min 2-75%, min 2.5-85%, min 2.6-95%, min 2.8-10%, min 3.5-75%, min 4-60%, min 5-30%). To wash the needle mixtures of water/methanol (70/30, v/v) containing 0.1% of formic acid (weak wash) and methanol/water/acetonitrile (40/30/30, v/v) containing 0.2% of formic acid (strong wash) were used.

Samples were kept at room temperature in the autosampler and 10 μL was injected in "partial loop with needle overfill" mode; the column was kept at 40° C.

The chromatographer was interfaced with a Waters Quattro Premier XE tandem mass spectrometer, equipped with an ESCi multi-mode ionization source (Waters Corporation, Milford, MA, USA) and operating in negative electrospray ionization (ESI+) mode. Analysis was performed in MRM (multiple reaction monitoring) mode, following two transitions for T3 (in brackets the relative optimized values of cone voltage and collision energy): 651.45>605.4 (33 v, 35 eV) and 651.45>478.7 (35 V, 30 eV).

The following parameters were applied in the tune page: capillary voltage was set at 3.00 kV and cone voltage at 30 V, while source and desolvation temperatures were 130 and 450° C., respectively. Nitrogen flow was set at 50 L/h on the cone and 500 L/h for desolvation; argon was used as collision gas at 0.35 mL/min. Data acquisition and processing were performed using MassLynx 4.1 software (Waters Corporation, Milford, MA, USA).

Calibration

Matrix-matched calibration curve was prepared using DMEM cell culture medium, that was spiked at 5 different concentrations of T3 (0, 10, 50, 100, 200 ng/mL).

Example 4 (In Vitro Testing)

Cell Culture

The murine macrophage cell line RAW 264.7 was purchased from the American Type Culture Collection (ATCC® TIB-71™). Cells were grown at 37° C. in DMEM high glucose medium (Thermo Fisher Scientific) supplemented with 10% heat-inactivated fetal bovine serum (FBS—Thermo Fisher Scientific), 1% penicillin/streptomycin (100 U ml-1/100 μg ml-1) (Thermo Fisher Scientific), in a humidified incubator of 5% $CO_2$. When 70-80% confluency was reached, cells were detached mechanically with the scraper and subcultured in 75 $cm^2$ flasks.

Treatments

In order to evaluate the bioactivity of ibuprofen and T3 released from electrospun PLLA fibres conditioned medium was prepared ad described below. Sterilized samples (1.5 cm×0.5 cm) of the scaffolds conjugated with ibuprofen (ibsc), scaffolds conjugated with T3 (T3sc), scaffolds conjugated with both ibuprofen and T3 (ibT3sc) and blank scaffolds (sc) were immersed in 1 ml of complete growth medium for 3 days at 37° C. with shaking (50 rpm). Medium with ibuprofen at final concentration 200 μM and T3 at 250 nM with blank PLLA electrospun scaffolds were incubated in the same conditions and served as control. At the end of the incubation, cells were seeded on 24-well plate with a density of 12000 cells/well. After 3-days confluent cells were treated for 24 h with conditioned medium and lipopolysaccharide (LPS) at the final concentration 500 ng/ml to stimulate inflammation. Table 1 described group's details. Three samples/group were analysed.

RNA Isolation and Semi-Quantitative Real-Time Polymerase Chain Reaction (qPCR)

At the end of the treatments total RNA isolation was performed with the RNeasy Micro kit (Qiagen) following the manufacturer's instructions. Total RNA was eluted in RNase-free water and concentration estimated through absorbance values at 260, 280 and 320 nm (Nanodrop 2000 spectrophotometer, Thermo Scientific). First-strand cDNAs were obtained using the iScript cDNA Synthesis Kit (Bio-Rad), incubating at 42° C. for 30 min. An RNA sample with no reverse transcriptase enzyme in the reaction mix was processed as a no-reverse transcription control sample. Semi-quantitative real-time PCR was performed using the CFX96 real-time PCR system (Bio-Rad). The reactions were performed in a final volume of 20 µl consisting of 1×SYBR Green qPCR master mix (Bio-Rad) and 0.4 µM forward and reverse primers. In order to avoid possible contamination of genomic DNA in isolated RNA, the sample with no reverse transcriptase enzyme was processed in parallel with the others and tested by real-time PCR for every pair of primers used. All primers used were designed using Primer Blast software (NCBI) and synthesized by IDT (Coralville). Used primer sequences are reported in Table 2. GAPDH was used as a housekeeping gene to normalize the amount of reverse-transcribed RNA used for PCR. Thermal profile of PCR reactions consisted first of a denaturation step (95° C., 2 min) and 40 cycles of amplification (95° C. for 15 s and 60° C. for 60 s). At the end of the amplification cycles, the melting curve of amplified products was performed according to the following temperature/time scheme: heating from 55° C. to 95° C. with a temperature increase of 0.5° C./s. Primer efficiency values for all primers were 95-102%. Relative quantification of the target genes expression was calculated using the comparative threshold method $2^{(-\Delta\Delta CT)}$. The primers used are also disclosed in Giardino L. et al. Glia 2006 September; (64(9):1573-89. doi:10.1002/glia.23025.

Statistical Analysis

Results were expressed as mean±standard error (SEM) and plotted on graphs. Statistical analyses were performed with Prism software (GraphPad) using Student's t-test and One-way ANOVA followed by Sidak's multiple comparisons test. Results were considered significant when the probability of their occurrence as a result of chance alone was less than 5% ($P<0.05$).

Example 5 (In Vivo Testing)

Animals

CD-Sprague Dawley (Charles River) female rats of 200-250 gr were used for this study. All animals were housed in pairs with standard bedding and diet. One week before surgery all animals were handled and accustomed to bladder manipulation.

Surgery and Animal Care

Animals (n=) underwent a contusive spinal lesion at the thoracic level (T9). Briefly, rats were anesthetized with isoflurane (1-3%) in 02 and treated before surgery with enrofloxacin and tramadol (4 mg/kg, s.c.). Laminectomy was performed at the T8-T10 vertebral level under aseptic conditions. The dura was carefully open and spinal cord was exposed. Contusive lesion of the spinal cord was obtained with Impact One impactor (Leica BioSystems) using a tip with different diameter (1.5 or 2 mm) and a force of 1 N (0.75 m/s) and 0 s of stance time, the depth of impact was 2 mm in order to reach ventral horns of gray matter. After performing spinal lesion Lidocaine was administered topically. Back muscles were sutured and the skin incision closed with wound clips. Upon completion of the surgery, animals received tramadol (4 mg/kg, s.c.) as an analgesic and enrofloxacin (4 mg/kg, s.c.) for 7 days to prevent infection. Bladders were expressed manually twice a day until voiding reflex returned (8-10 days). Animals were housed in single cage for the first week after surgery.

Evaluation of rats wellness was performed using a clinical score described by Ramsey et al. (2010), in particular animal weight was the first parameter monitored after spinal cord lesion. Clinical score was evaluated daily for the first two week, then once a week until the day of sacrifice. In case of infection of lower urinary tract, animals were treated twice a day with enrofloxacin (4 mg/kg, s.c.) for three days.

At the time of sacrifice, CSF and blood were collected. Then tissues, lesioned, supra and sub lesion tracts of the spinal cord (SC-L, SC-UL, SC-DL), motor cortex (CTX-M), basal ganglia (BG) were dissected, weighed, immediately snap frozen and stored at −80° C. till used. SC-L dedicated to IHC was fixed as described below. SC-L for citofluorimetry and sinaptosomes analysis were dissected and immediately used for analysis. Blood was collected in EDTA-K2 vacutainer tubes and centrifuged at 3000×g for 10 min at 4° C. and plasma was removed, aliquoted in polypropylene tubes and stored at −80° C. till used. CSF was also collected in polypropylene tubes and immediately stored at −80° C. till used.

Treatments and Electrospun Biomaterials Implantation

Systemic treatment was administered daily via sub-cutaneous injections starting after two hours after spinal lesion and for the successive 10 days. Animals were treated with 60 mg/kg of ibuprofen once a day and 10 ug/kg of T3 twice a day (Fernandez et al., 2004; D'intino et al, 2011; Dell'Acqua et al, 2012).

Implantation of ibuprofen and T3 conjugated scaffolds was performed after spinal cord lesion. Electrospun was placed upon the spinal cord, bent over it and then fixed with BioGlue (CryoLife) at the spinal process of adjacent vertebrae.

Functional Locomotion and Gait Analysis

Evaluation of hind limb functional locomotor loss was performed with BBB score (Basso et al.) three days post lesion and if lesioned animals received a score greater than 1 were discarded from the analysis (4 animals in Lesion 8 days group and one animal in Lesion 45 days group were excluded from analysis). BBB score was repeated once a week after surgery in both lesion and sham animal groups to asses spontaneous motor recovery.

Gait analysis was performed with CatWalk (Noldus) automatized system. Animals were trained before surgery to walk repeatedly along the platform, then tested two days before spinal cord lesion and once a week after lesion. All animals undergo 5 compliant runs, as defined by instrument parameters (run duration from 0.5 s to 7 s), for each time point and means of all parameters were calculated by CatWalk software. Gait analysis was performed on 11 different parameters, divided in 4 categories: Spatial Parameters (Print Area, Max Contact Area, Base of Support); Kinetic Parameters (Stand Time, Swing Time, Swing Speed, Single Stance); Comparative Parameters (Stride Length, Step Cycle); Coordination Parameters (Duty Cicle, Step Sequence Regularity Index). All parameters were analyzed for both hind paws and front paws (represented as mean of right paw and left paw).

Histochemistry

At the day of sacrifice rats were perfused with 4% paraformaldehyde and picric acid saturated aqueous solution in 0.1 M Sorensen buffer pH 7, then spinal cord tissue was dissected and post-fixed for 24 hours, then washed with Sucrose 5% O/N. 14 µm thick sagittal and coronal sections were then prepared (Leica CM1950) and processed for histochemistry staining. Toluidine blue and Hematoxilin/Eosin were performed for evaluation of lesion area and inflammatory infiltrate. For the definition of lesion area, section were captured with Nikon Microphot—FXA equipped with a CCD camera Nikon DXM1200F (Nikon) and then measured with Photoshop (Adobe), all images were capture with a 4× magnification of the objective and reconstructed with Photoshop's photomerge function. Lesion area was then determined for each reconstructed section with ImageJ software (NIH) as number of pixels occupying the lesion site and to obtain the ratio between lesion and healthy tissue, total section areas were measured for each section. 3D reconstruction was obtained align different levels of the same spinal cord (sampling step 210 µm).

Total RNA Isolation, Reverse Transcription and PCR-Arrays.

Right CTX-M, SC-DL, SC-UL and BG were homogenized and total RNA isolation was performed using RNeasy Microarray Tissue Mini Kit (Qiagen). Total RNA was eluted in RNase Free Water and using a spectrophotometer (Nanodrop 2000, Thermo Scientific), absorbance values were measured and purity (A260/A280) evaluated. RNAs were pooled for each group to obtain a total amount of RNA of 0.5 µg. Genomic DNA was digested using GE Buffer (Qiagen) for 5 minutes at 42° C. and then retrotranscribed using the RT2 First Strand Kit (Qiagen) and thermal cycler for 15 minutes at 42° C. followed by 5 minutes at 92° C. for enzyme inhibition. Synaptic Plasticity analysis was performed using Rat Synaptic Plasticity PCR Array (PARN-126ZD—Qiagen), a specific panel of 84 genes involved in Rat Synaptic Plasticity (Table 1). Real time amplification of cDNA pools was achieved with CFX96 Real Time PCR System (Biorad). In order to check for possible contamination of genomic DNA, the Array contains internal controls. Thermal profile of PCR reactions was performed as follow: an activation step of Taq polymerase (95° C., 10 min) and 40 cycles of denaturation (95° C., 15 sec) and annealing/extension (60° C. for 1 min and 30 sec). At the end of the amplification cycles the dissociation curve was obtained by following a procedure consisting of first incubating samples at 95° C. for 1 min to denature the PCR-amplified products, then ramping temperature down to 65° C. and finally increasing temperature from 65° C. to 95° C. at the rate of 0.5° C./s, continuously collecting fluorescence intensity over the temperature ramp. Analysis of genes expression of the array was performed using the RT2 Profiler PCR Array Data Analysis version 3.5 (SABiosciences), previously expression threshold was set in order to analyze only linear expression and maximum Ct was set at the value of 35. Gene expression was normalized on automatically detected reference genes suggested by the software.

Citofluorimetry Analysis

After SC-L collection, tissues were dissociated in single cells with Multi Tissue Dissociation Kit 1 (Miltenyi Biotech) using GentleMACS Dissociators (Miltenyi Biotech) for 45 minutes. Tissue debris were removed using Debris Removal Solution (Miltenyi Biotech) in order to eliminate myelin and cellular debris. Cells were marked with a panel of antibodies (Table . . . ) in order to evaluate inflammation, oligodendrocite population and vitality of cells.

MACSQuant Flow Cytometer (Miltenyi Biotech) was used to separate and count cell populations marked with specific antibody. Compensation of instrument channels were performed before sample analysis in order to prevent laser overlay during sample reading.

Glutamate Release in Synaptosomes

Crude synaptosome (P2) fraction was prepared from the spinal cord. Briefly, on the day of the experiment, a lightly anesthetised animal was sacrificed by decapitation and the cerebellum was dissected out from the brain. The tissue was then homogenised in ice-cold buffered (pH 7.4) sucrose solution (0.32 m). After the homogenate centrifugation (10 min; 2500 g, 4° C.), the supernatant was collected and the synaptosomes were isolated by centrifugation (20 min; 9500 g, 4° C.). The P2 pellet fraction was resuspended in 5 ml of Krebs solution (mm: NaCl 118.5, KCl 4.7, CaCl2) 1.2, KH2PO4 1.2, MgSO4 1.2, NaHCO3 25, glucose 10; gassed with 95% O2/5% CO2) (Chiodi et al. 2012).

After their preparation, the synaptosomes were maintained in warm condition (37° C.) for 20 min. Thereafter, identical aliquots (0.5 ml) of synaptosomal suspension were distributed on microporous filters, placed at the bottom of a set of parallel superfusion chambers, maintained at 37° C. and continuously perfused with aerated (95% O2/5% CO2) Krebs solution (0.3 ml/min). After a 30-min wash-out period, nine consecutives 5-min fractions were collected. In details, after the collection of three basal samples, synaptosomes were depolarized with 15 mm K+ for 90 seconds. In each sample, GABA and glutamate levels were simultaneously measured by HPLC coupled with fluorimetric detection. Thirty microlitres per sample were transferred into glass microvials and placed in a temperature-controlled (4° C.) Triathlon autosampler (Spark Holland, Emmen, The Netherlands). Before the injection, the system added 30 µl of o-phthaldialdehyde/mercaptoethanol reagent to each sample and, after 60 seconds of reaction, 40 µl of the mixture was injected onto a Chromsep analytical column (3 mm inner diameter, 10 cm length; Chrompack, Middelburg, The Netherlands). The column was eluted at a flow rate of 0.52 ml/min (Beckman 125 pump; Beckman Instruments Indianapolis, IN, USA) with a mobile phase containing 0.1 m sodium acetate, 10% methanol and 2.2% tetrahydrofuran (pH 6.5). Glutamate and GABA were detected by means of a Jasco fluorescence spectrophotometer FP-2020 Plus (Jasco, Tokyo, Japan). The retention times of glutamate and GABA were ~3.5 and ~15.0 min, respectively.

The GABA and glutamate efflux were expressed as pmol/min/g of protein while K+-evoked GABA and glutamate efflux were expressed as percent increase over the respective spontaneous efflux (calculated by the mean of the two fractions collected prior to the depolarising stimulus). Protein was determined according to Bradford (1976).

Results

1. Material Design and Fabrication

Determination of T3 Content into the PLLA Electrospun Fibers

Around 10 mg of fiber, accurately weighed, was extracted with 4 mL of methanol and left in a ultrasonic bath for 15 minutes. Than the mixture was centrifuged at 7250 rpm for 5 minutes. The supernatant was collected and the fiber was re-extracted with the same procedure two more times. The three extracts were collected and concentrated in volumetric flash at 5 mL. 10 µL were diluted with 990 µL of methanol containing 0.1% of formic acid and injected in LC-MS/MS system.

The quantification was carried with calibration curves in methanol spiked at 6 different concentrations of T3 (0, 100, 200, 300, 400, 500 ng/mL) freshly prepared each analysis day.

Determination of IBU Content into the PLGA and PLLA Electrospun Fibers

PLGA: a part of fiber, accurately weighed, was dissolved in 2 mL of ACN, stirred to facilitate the dissolution of the active ingredient and centrifuged for 10 minutes to separate the drug from the polymer. Then the solution was diluted 1:10 with a PBS:ACN (1:1) solution; if necessary, dilutions were made to get a concentration in the range of 0.05-20 µg/ml. Then, the drug content of the solution was assayed by HPLC, as reported in the previously Section.

PLLA: a part of fiber, accurately weighted, was dissolved in 2 mL of ACN:DMSO (3:1 v/v), warmed up and sonicated for 15 minutes, finally the solutions were centrifuged for 10 minutes; if necessary, dilutions were made to get a concentration in the range of 0.05-20 µg/ml. Then, the IBU content of the solution was assayed by HPLC, as reported in the previously Section.

Finally, the encapsulation efficiencies (EE) of the PLGA and PLLA fibers were calculated as follows:

$$EE\ (\%) = (Wa/Wt) \times 100$$

where Wa is the actual drug content and Wt is the theoretical drug content.

In Vitro Drug Release

A portion (part) of fiber, accurately weighed, was poured in a tube, filled with 10 mL of PBS at pH 7.4. The tubes were horizontally shaken at a temperature of 37° C. At predetermined time intervals (from 1 hour to 21 days), the release medium was withdrawn and completely replaced with 10 mL of fresh buffer solution.

For IBU determination, the withdrawn fluid samples were then acidificated with HCl conc, filtered (0.4 um NY filter), diluted if necessary, then the drug content was analyzed by HPLC as described above. The release tests were performed at least in triplicate and the mean±SD was reported.

For T3 determination samples have been subjected to extraction protocol e purification for the analysis by LC-MS/MS (see paragraph above).

Validation of the Analytical Procedures: Ibuprofen

In order to optimize the HPLC method, different mobile phase ratios and different pH conditions were tested to obtain a sharp and symmetrical peak and short retention time. In particular the following volumetric ratios CH3CN:NH4H2PO4 (50:50, 55:45 e 57:43 v/v) in an isocratic elution were evaluated. For this purpose a standard solution of ibuprofen was prepared and used for the analyses.

The standard solution (10 µg/mL) was injected using at different mobile phase ratios. Increasing the percentage of organic phase, the retention time shifted from 7.1 to 5.2 minutes; in all cases the IBU peak is baseline resolved and showed good symmetry, the optimal condition was obtained using the 57:43 v/v ratio.

In addition, four different values of pH (2.5, 3.0, 3.5 and 7.4) were investigated. Under these conditions the shape of the peak and his retention time did not show significantly differences. Therefore, the CH3CN:NH4H2PO4 ratio (57:43 v/v) pH 3 (adjusted using ortho phosphoric acid) was used to analyze all samples.

In order to obtain a calibration curve, IBU standard solutions in the range of 0.05-20 µg/ml were used. Each measurement was performed in triplicate. Quantitative evaluation was carried out by integration of the peak areas and fitting these values into the calibration curve: the mean linear regression equation y=47936x+860.4 and a correlation coefficient r2=0.999 were obtained. This value of correlation coefficient indicated good linearity of calibration curve 1, 2 (1. International Conference on Harmonisation (ICH), 2005. Harmonised Tripartite Guideline: Validation of Analytical Procedures: Methodology (Q2B), 2005. 2. United States Pharmacopeia (USP) 34 (NF 29), Chapter 621, Edition 2011).

The limit of detection calculated as LOD=3σ/s was 6.2 ng/mL and the limit of quantification calculated as LOQ=10σ/s was 20.8 ng/mL.

The method was also evaluated for the determination of IBU in presence of T3 (hormone thyroid) and in samples consisting of complete DMEM containing 10% of FBS (Dulbecco's Modified Eagle Medium+10% Fetal Bovine Serum DMEM-FBS). For this purpose, a standard solution (PBS pH 7.4) containing a mixing of IBU (10 µg/mL) and T3 (20 µg/mL) were analysed. The obtained chromatograms did not present additional peak at the retention time of IBU. Furthermore, to test the use of the analytical method also for the determination of IBU in culture medium, different samples consisting of complete DMEM (DMEM+10% FBS) and samples of DMEM (without FBS) were initially analysed. In both cases, the chromatograms did not show the presence additional peaks at IBU retention time. Subsequently, complete DMEM solutions containing known concentrations of IBU (1 and 10 µg/mL) were prepared. The results showed a recovery of more than 96% for both concentrations.

Validation of the Analytical Procedures: T3

Different chromatographic conditions were tested to obtain an optimal retention and a good separation of the analyte from the matrix interfering compounds in a reasonable analysis time. The chosen chromatographic gradient allowed a good elution of T3 in 1.9 min, with better-shaped and more symmetrical peak.

The mass spectra of T3 was acquired after direct infusion of the tuning standard solutions. The higher response was obtained using an ESI operating in positive ionization.

T3 was identified on the basis of retention time, the presence of two specific mass transitions and ion ratio of these product ions.

The specificity was evaluated by checking the ion chromatograms of 10 blank samples of culture medium extracted and analyzed with the above-mentioned method for potential co-eluting interfering compounds, which can impair interpretation at the specific retention time of the analytes.

The linearity of the method was assessed with matrix-matched calibration curves freshly prepared each analysis day. The regression lines obtained were all satisfactory, with a coefficient of determination (r2) always higher than 0.98, in the range from 0 to 200 ng/mL.

The accuracy of the determination was assured by preparing and analyzing twice (at the beginning and at the end of each batch of analysis) the calibration curve in cell culture medium.

In Vitro Testing: Drug Content and Release Characterization.

T3 Content in the Electrospun in PLLA Fibers

T3 content in PLLA fibers loaded with two drugs (IBU and T3) was determined in five samples. The average content of T3 was 1.73±0.41 µg/mg of fiber.

IBU Content and Release in the Electrospun Fibers.

The majority of fibers containing only IBU had an actual drug content very close to the theoretical one, therefore the EE % were around 100% for almost all the samples. Moreover the drug distribution in the fibers was homogeneous. These results demonstrated that the final operating parameters utilised for the production of the IBU loaded fibers were correct.

On the contrary, the actual IBU content in the fibers loaded with two drugs (IBU and T3) was inferior than the theoretical one (3.4% vs 5.0%); moreover the drug distribution in the fibers was non homogenous. This results can be explained considering that the two-syringes process (FIG. 1) had much higher variability, due to charge repulsions in the process.

The fibers obtained using the PLGA 50:50-IBU conjugated showed a drug content of 2%.

Figure 2:
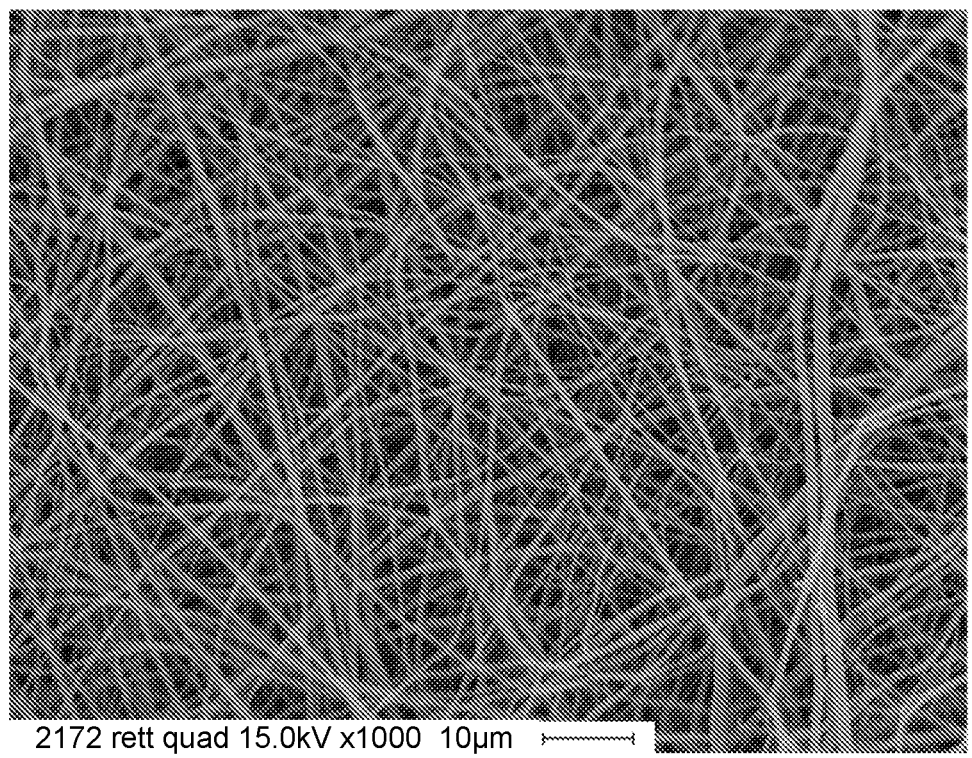
FIG. 2 shows a scanning electron microscopy (SEM) image of the electrospun polymeric fibers according to one embodiment of the invention.
Figure 3:
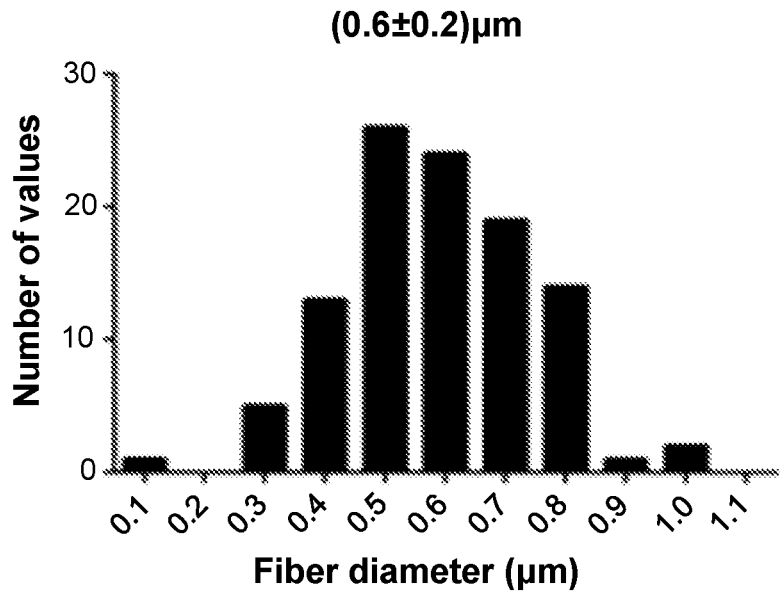
FIG. 3 shows the fiber diameter distribution of the electrospun fibers according to one embodiment of the invention.

Drug release from implantable polymer-based scaffolds, such as the electrospun fibers, is strongly influenced by scaffold proprieties (FIGS. 2 and 3).

Figure 14:
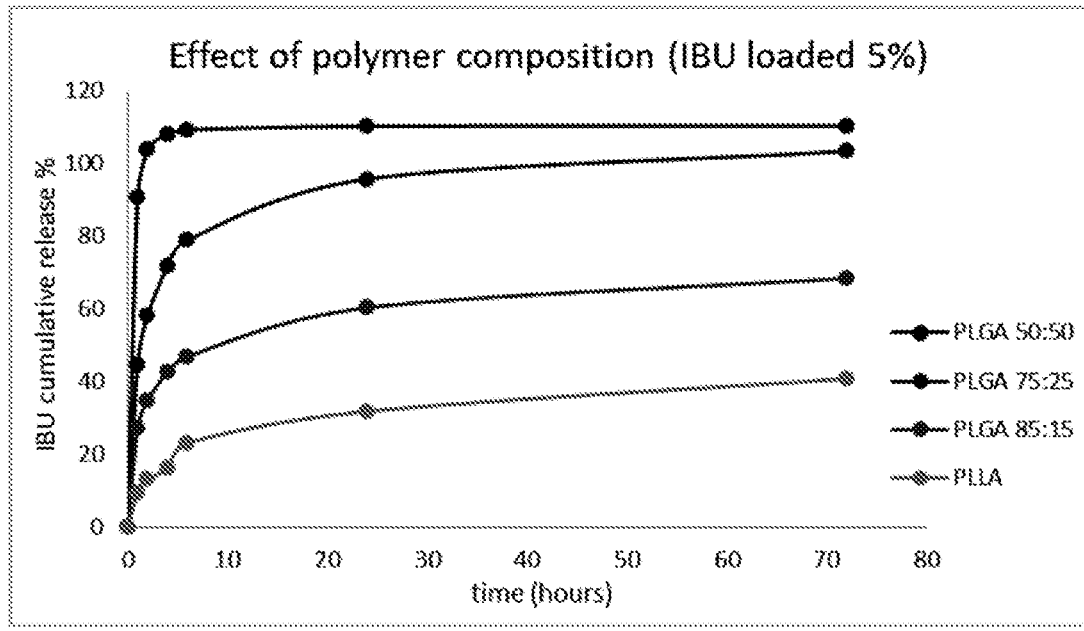
FIG. 14 shows the best polymer chemistry for the drug release profile required for the purpose of the invention

In this study, the effect of:
(i) polymer composition (lactide/glycolide ratio);
(ii) amount of IBU loaded and drug incorporation method (physical incorporation or polymer-drug conjugation);
(iii) morphology (nano or micro diameters of the fibers).
(iv) Effect of polymer composition (lactide/glycolide ratio) on the IBU release profiles has been evaluated (FIG. 14).

The IBU release results showed that the polymer composition (lactide/glycolide ratio) had a pronounced effect on the IBU release from the fibers. Therefore, by selecting the polymer, it is possible to modulate the drug release rate. The drug release rate increased, increasing the ratio of PGA (more hydrophilic) respect to PLA. In any case, PLGA 50:50, PLGA 75:25 and PLGA 85:15 fibers showed a pronounced burst effect, releasing around the 80% of the drug in 24 h. PLLA systems exhibited better performance; in particular the 5% IBU-loaded PLLA fibers released only the 20% of drug in 24 h, followed by a controlled IBU release phase.

Therefore, the system based on PLLA and containing 5% IBU was selected for the next step.

Figure 15:
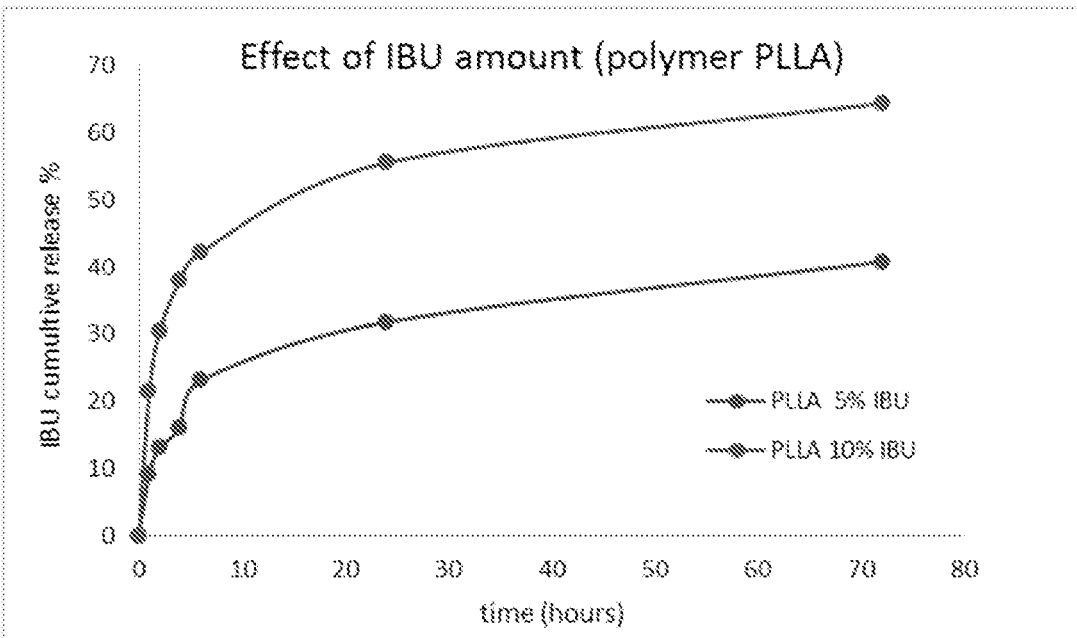
FIG. 15 shows the best drug concentration for the polymer fabrication to obtain the drug release profile required for the purpose of the invention

(ii) Amount of IBU Loaded and Drug Incorporation Method (Physical Incorporation or Polymer-Drug Conjugation) (FIG. 15).

The effect of the amount (5% and 10%) of IBU loaded on the release profiles was studied for blended fibers produced using PLGA and PLLA polymers. The results showed an increasing of the burst release of IBU by increasing the drug amount. This effect is more evident in PLLA systems respect to PLGA ones. Fibers produced using the PLGA 50:50-IBU conjugated released only around the 2% of IBU in 21 days.

(iii) Morphology (Nano or Micro Diameters of the Fibers)

Figure 16:
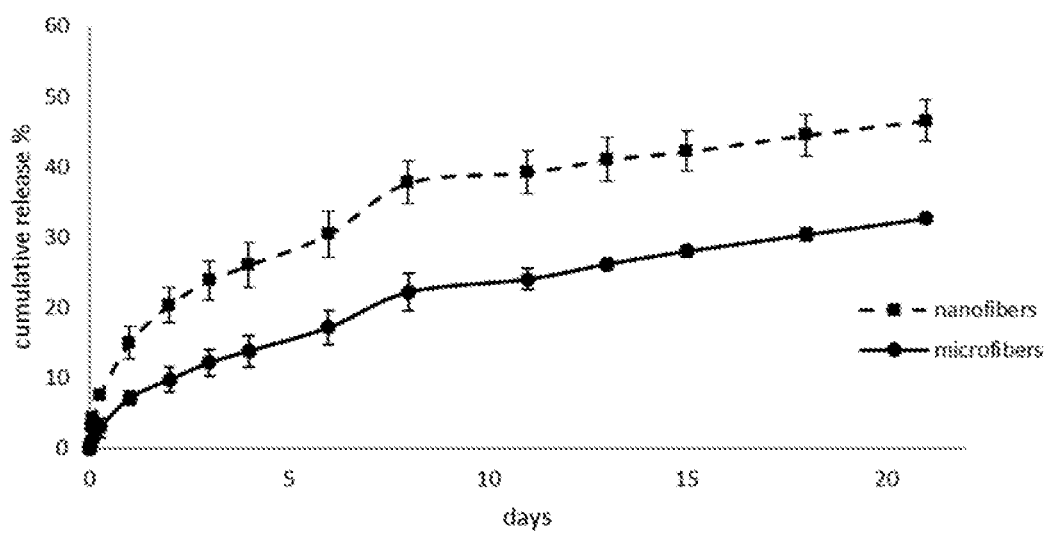
FIG. 16 shows the best fibres diameter for the polymer fabrication to obtain the drug release profile required for the purpose of the invention.

In order to study the effect of the fiber size on the drug release, micrometric and nanometric fibers (based on PLLA and containing 5% IBU) were produced. Both materials (micro and nano) showed a similar release profiles, however the difference in fiber size affected the amount of drug released. As expected, the percentage of the drug release from nanometer fibers was higher than from the microfibers (42% and 28% after 14 days, respectively) (FIG. 16).

Based on the in vitro IBU release results, the system based on 5% IBU loaded PLLA was selected for the production of electrospun fibers containing both IBU and T3. The final system showed the desired controlled drug release profile, delivering the target amount of IBU in the prefixed time.

T3 and IBU Release in the Electrospun Fibers.

Figure 4:
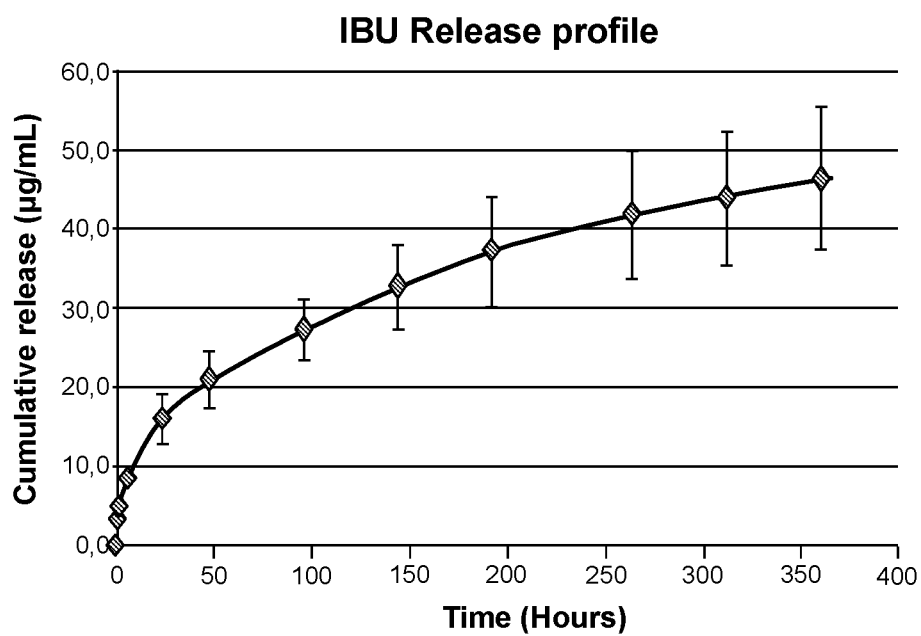
FIG. 4 shows the cumulative release of ibuprofen obtained over the expected delivery time (15 days) according to one embodiment.
Figure 5:
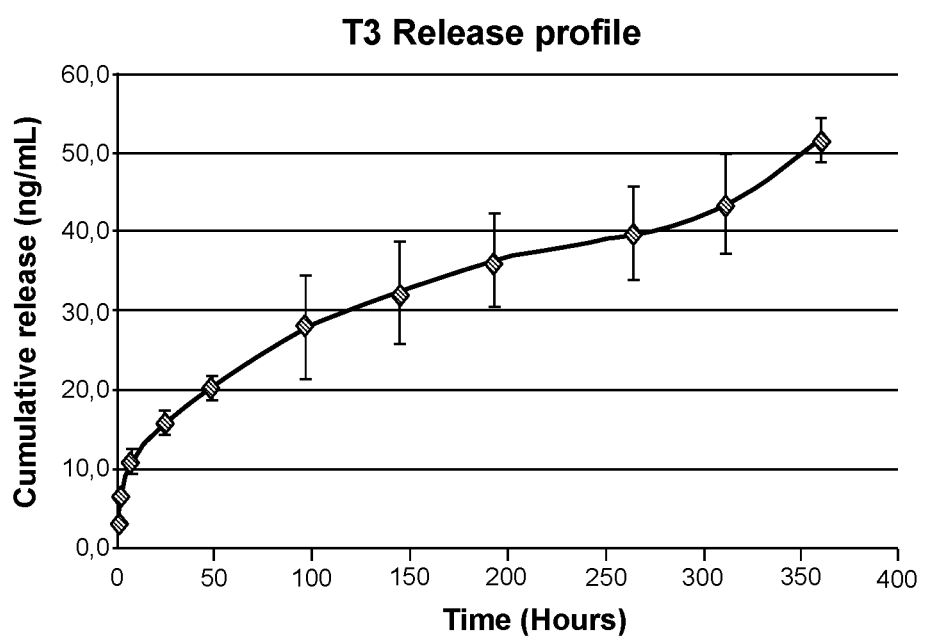
FIG. 5 shows the cumulative release of T3 obtained over the expected delivery time (15 days) according to one embodiment.

The cumulative release of T3 and IBU over 14 days (350 hours) is presented in FIGS. 4 and 5. The in vitro release studies confirm that the PLLA scaffold guarantee the expected drug delivery, in term of drugs concentration and time of delivery.

Quantification of T3 in DMEM Cell Culture Medium Conditioned by PLLA Polymer

The cell culture medium samples, conditioned for the in vitro tests, have been subjected to extraction protocol e purification for the analytical determination of T3 by LC-MS/MS. The average concentration measured (n=3) was 119.0±48.7 ng/mL.

In Vitro Testing: Efficacy

The following conditions were tested:

| Group description | Abbreviation |
| --- | --- |
| Blank scaffold (control without LPS stimulation) | sc |
| Blank scaffold + LPS (control with LPS stimulation) | sc LPS |
| Scaffold loaded with ibuprofen + LPS | ibsc LPS |
| Scaffold loaded with T3 + LPS | T3sc LPS |
| Scaffold loaded with ibuprofen and T3 + LPS | ibT3sc LPS |
| Blank scaffold with ibuprofen in the solution + LPS | sc + IBU LPS |
| Blank scaffold with T3 in the solution + LPS | sc + T3 LPS |
| Blank scaffold with ibuprofen and T3 in the solution + LPS | sc + IBU + T3 LPS |

Figure 6:
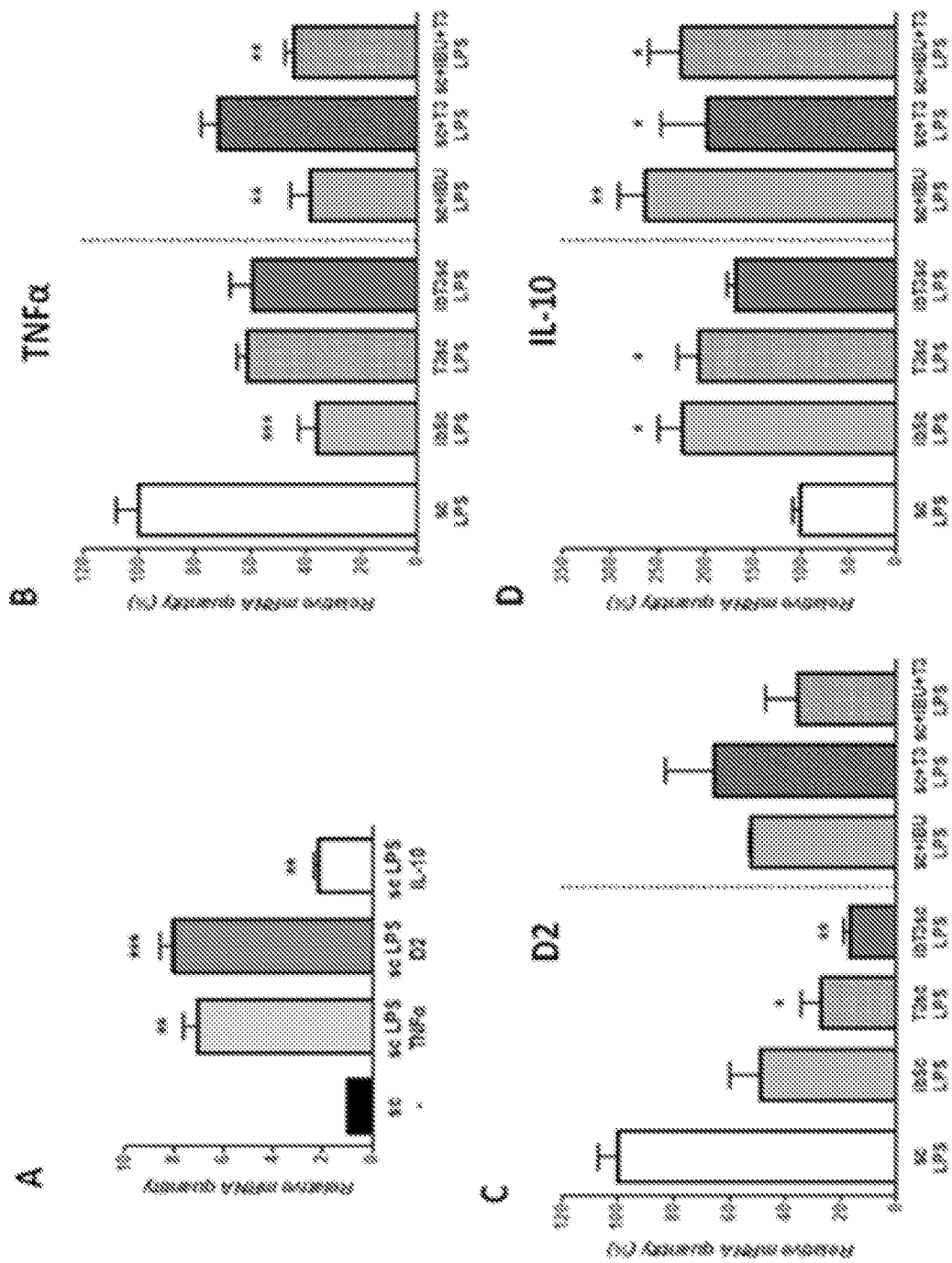
FIG. 6 shows the in vitro efficacy test on LPS stimulated RAW cells, in the presence of the culture medium conditioned to mimic the cumulative T3 and IBU release, proving that that the conditioned medium reverts the molecular effect triggered by LPS according to one embodiment.

In order to access the efficacy of biomaterials in vitro, gene expression analyses were performed to evaluate if drugs released from scaffolds as well as solubilized drugs are able to change mRNA profiles of some specific pathways-related genes upon LPS stimulation. Genes codifying for pro- (TNFα) and anti-inflammatory (IL-10) cytokines as well as for marker of thyroid hormone pathway deiodinase 2 (D2) were used. Administration of 500 ng/ml LPS for 24 h results in the increase of TNFα, D2 and IL-10 about 7-, 8- and 2-fold over the basal level, respectively (FIG. 6 A). In fact, non-stimulated macrophages express those genes in a negligible level (data not shown).

After cell treatments with medium containing ibuprofen and T3 released from the PLLA scaffolds, down-regulation of TNFα and D2 was observed for all scaffold's groups respect to LPS-stimulated control (sc LPS) (FIG. 6 B, C). The TNFα mRNA level decreased in a highest extent (64%) for the scaffold conjugated with ibuprofen (ibsc) compared to sc LPS (p=0.0006) and it was comparable to the control with ibuprofen added as a solution (SC+IBU, p=0.0011, FIG. 6 B). This effect indicates that 3 days of ibsc incubation in the cell culture medium can provide an amount of ibuprofen (around 32 µg), which is effective to significantly inhibit the inflammatory action.

Another important marker of inflammation investigated in this study was deiodinase 2, which was highly up-regulated in LPS-activated macrophages compared to non-stimulated control (p=0.0006, FIG. 6 A). Additionally, it was significantly down-regulated after treatments with medium enriched in ibuprofen and T3 released from the scaffolds with statistically significant differences for T3sc and ibT3sc groups respect to sc LPS (p=0.013 and p=0.001 respectively, FIG. 6 C). D2 down-regulation of 83% for ibT3sc compared to the 73% for T3sc and 50% for ibsc suggests on synergistic anti-inflammatory effect when both molecules are present (FIG. 6 C).

The last analysed cytokine was the anti-inflammatory IL-10 which represented low mRNA level after only LPS administration and its expression significantly increased in all three scaffolds group confirming anti-inflammatory effect of ibuprofen and T3 released from the scaffolds on LPS-activated macrophages (FIG. 6 D).

In Vivo Testing

The Traumatic Spinal Cord Injury Model

Figure 7:
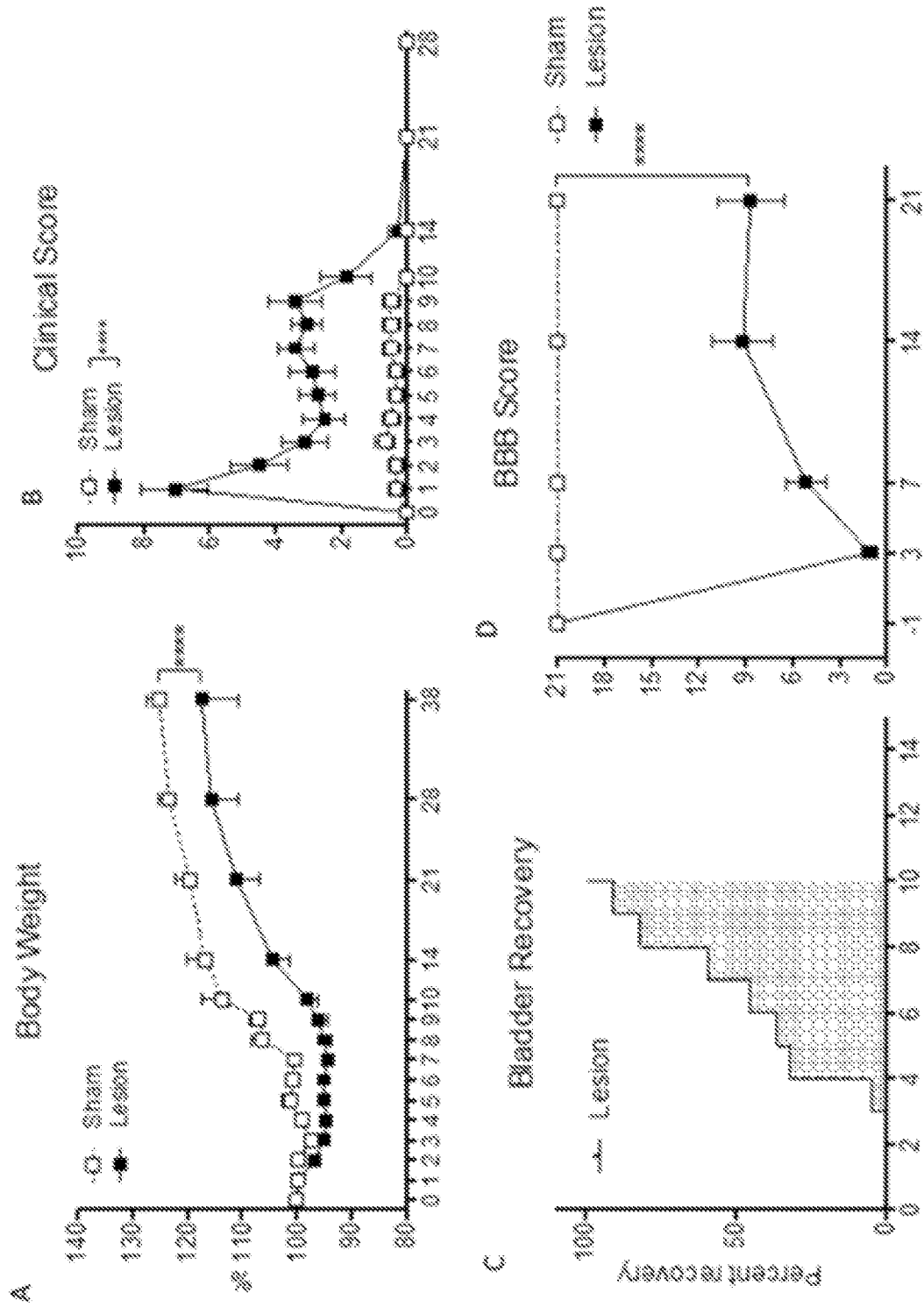
FIG. 7 shows the functional parameters used for the efficacy test in vivo, in the rat model for the contusive spinal cord injury according to one embodiment.
Figure 8:
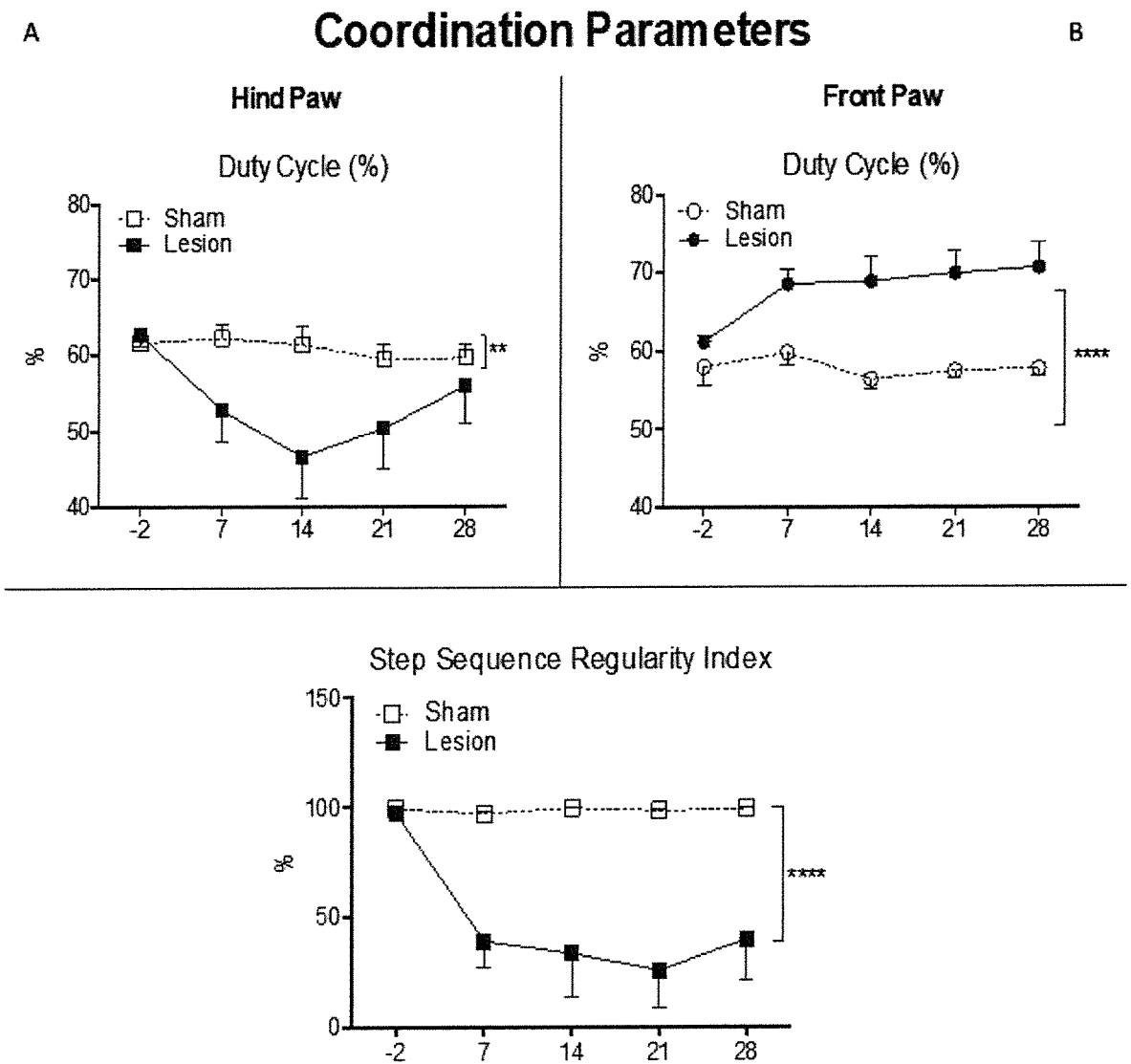
FIG. 8 shows the gait parameters used for the efficacy test in vivo, in the rat model for the contusive spinal cord injury according to one embodiment.

The rat contusion model has been extensively characterized, and the most significant parameters for efficacy studies are presented in FIG. 7.

Figure 13:
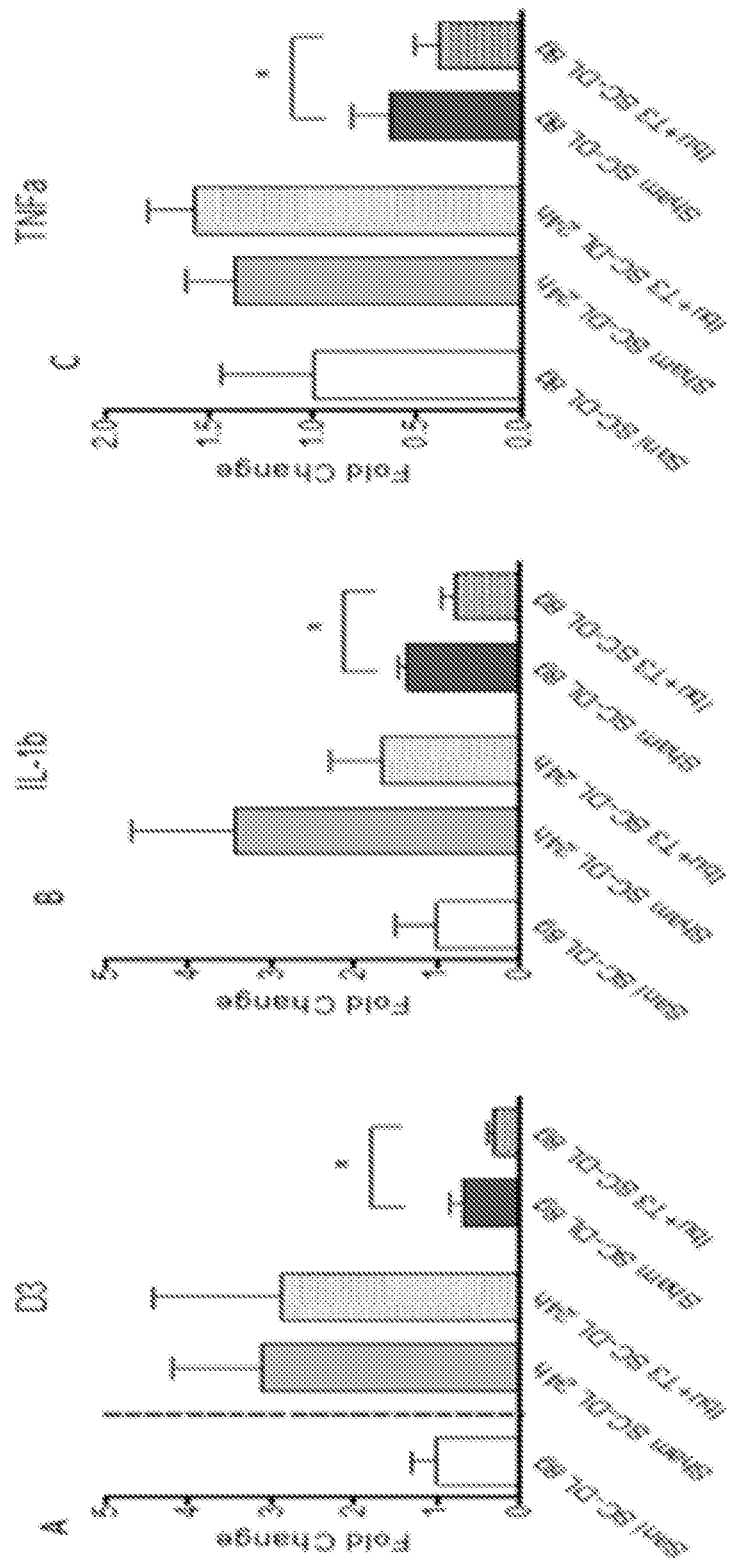
FIG. 13 shows the mRNA expression level of molecules involved in inflammation and remyelination in the spinal cord of lesioned and implanted rats, proving that the invention counteracts the lesion-induced changes, decreasing inflammation and anti-remyelination markers
Figure 17:
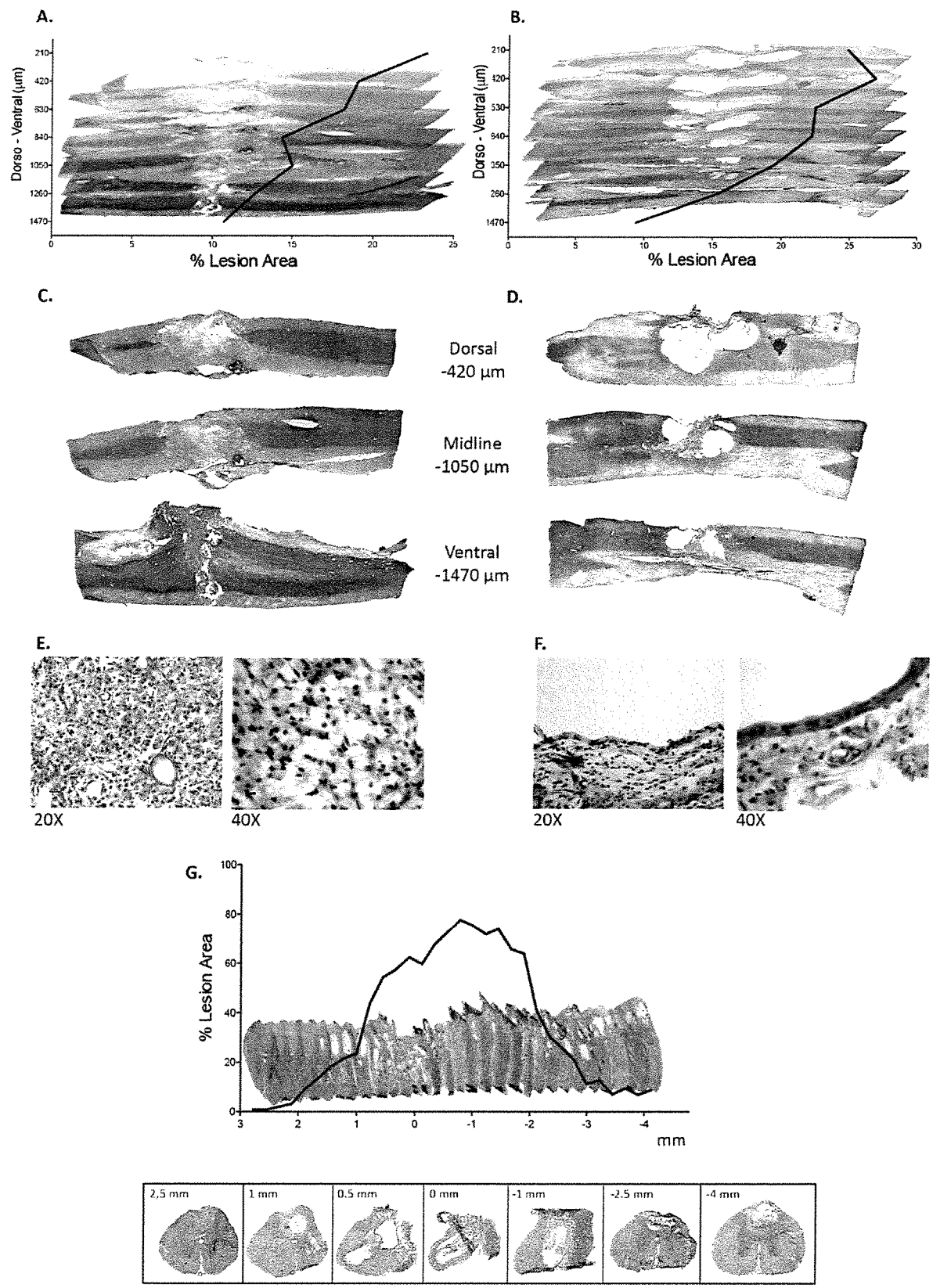
FIG. 17 shows the estimated lesion volume.

Body weight gain after surgery procedure in experimental animal, expressed as % changes respect to pre-surgery bw: lesioned animals show a remarkably decrease in body weight after contusion, which is partially recovered over the time. Daily clinical score evaluating behaviour, wound closure, infections and mass index: lesioned animals display higher clinical score in the first two weeks after surgery. Bladder function recover, showing the this function recovers over a time span of 6 days (from 4 to 19 days). Basso-Beattie-Bresnahan 21 point score for evaluation of locomotor recovery after spinal lesion: lesion group animals show a substantial decrease in locomotion after spinal cord injury, which is partially recovered over the time. Selected parameter of the gait analysis performed by CatWalk apparatus are presented in FIG. 13. In particular, coordination parameters (Duty Cycle, Step Sequence Regularity Index) describing the ability of animals in coordinating movements indicates that injured animals show differences in all parameters analysed compared to sham animals. Notably, the duty cycle is recovered. The lesion volume has been also estimated, and results are presented in FIG. 17

Control Treatment: Systemic Administration

Figure 9:
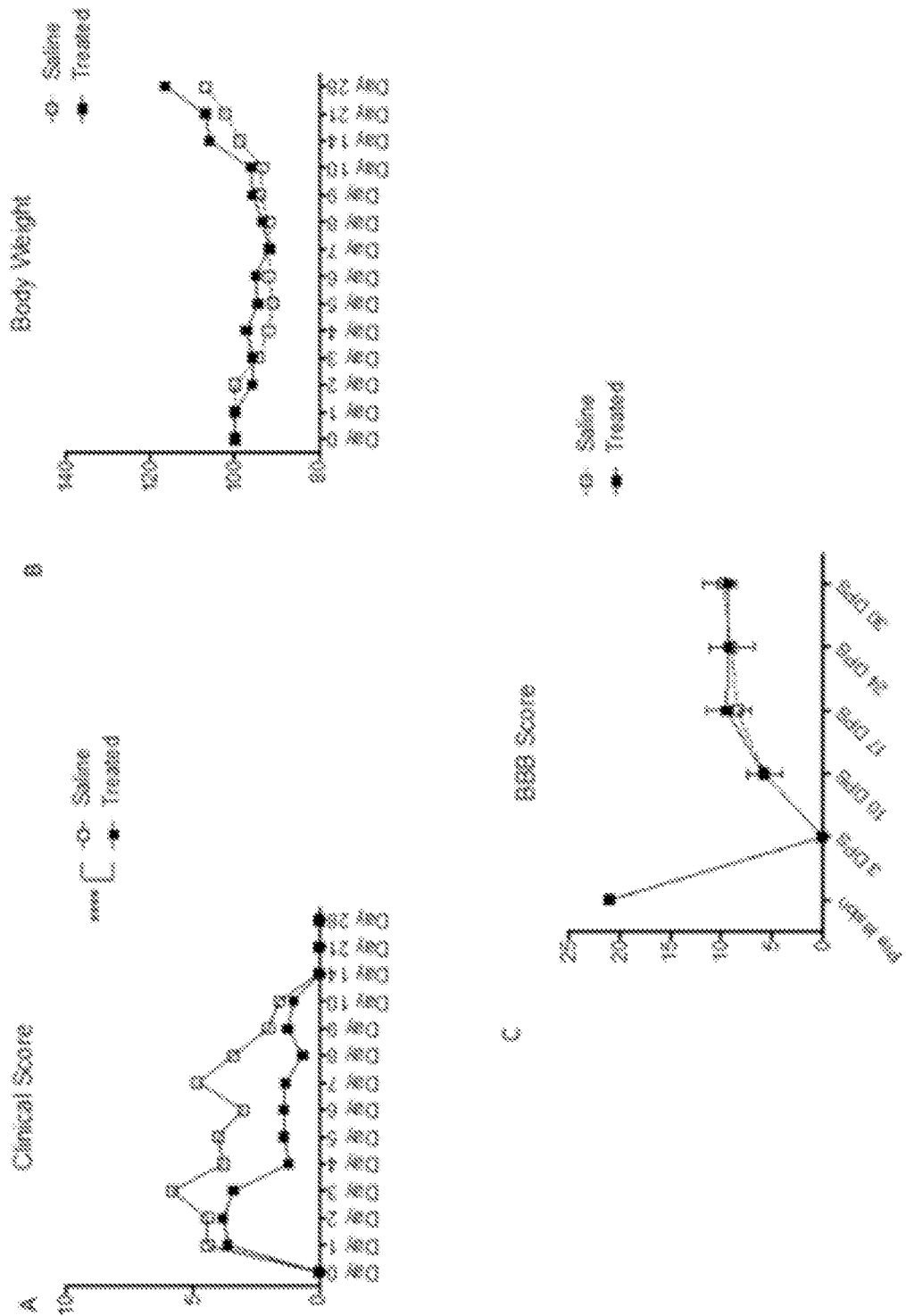
FIG. 9 shows the effect of the systemic administration of the drug combination used according to one embodiment of the invention.

In order to prove that the local delivery system is more effective than systemic administration, we performed an efficacy study after systemic administration of IBU (60 mg/kg/day, 10 days) and T3 (10 g/kg, twice day, 10 days). We observed a slight improvement of general conditions (clinical score), but no effects on locomotion recovery (FIG. 9).

Exploratory End-Points: Impact of the Step1 on Locomotion

Glutamate Release.

Figure 10:
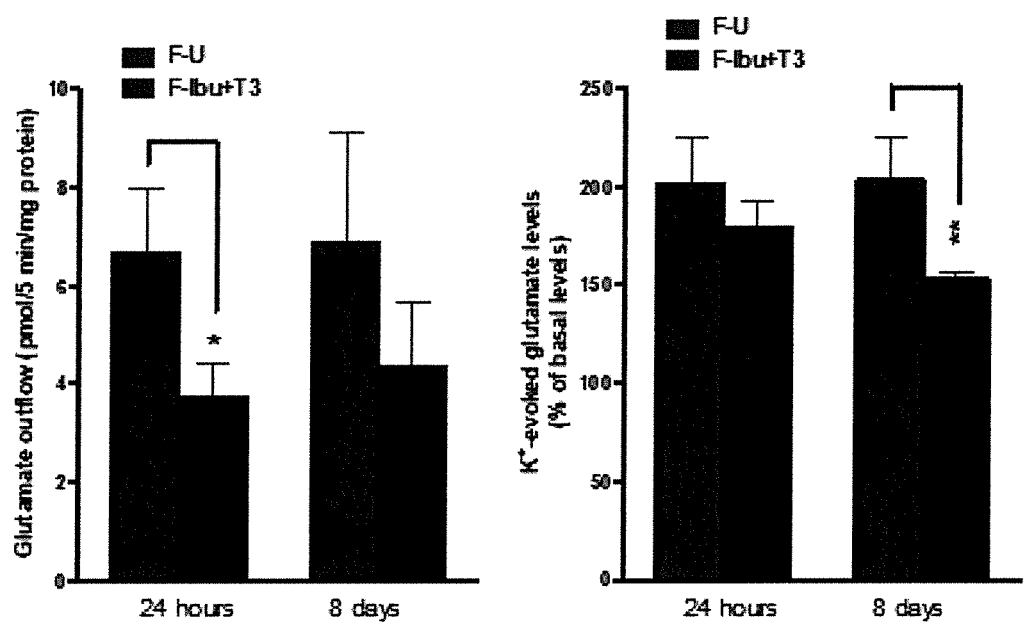
FIG. 10 shows the inhibition of glutamate release from synaptosomes obtained by the spinal cord of rat implanted with the invention, in comparison with the polymer, alone, proving the efficacy in blocking the primary event that triggers secondary neurodegeneration.
Figure 11:
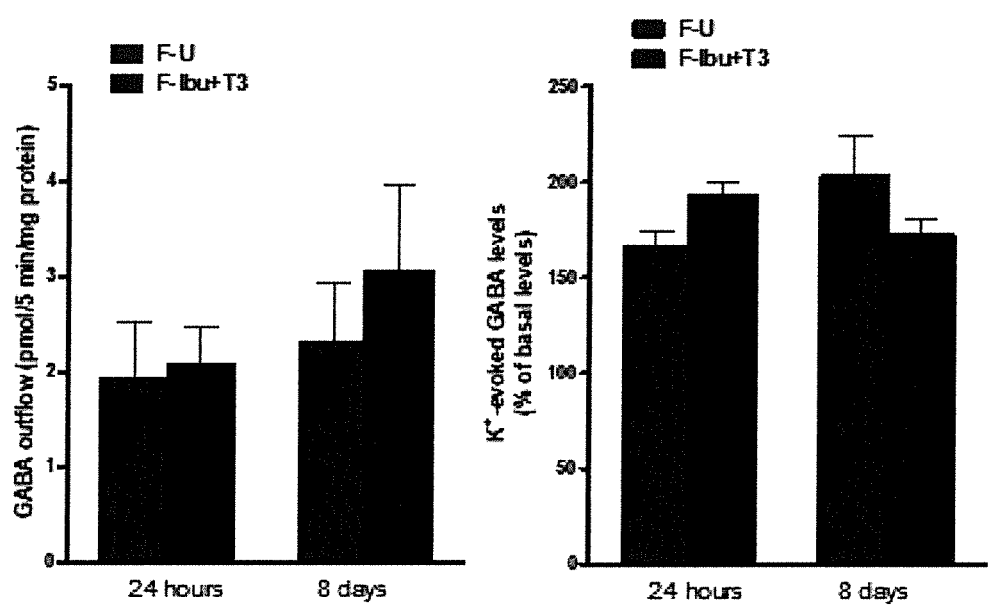
FIG. 11 shows the inhibition of GABA release from synaptosomes obtained by the spinal cord of rat implanted with the invention, in comparison with the polymer, alone, to prove the specificity on glutamate release

The first event in triggering secondary degeneration is the glutamate release. We then measured glutamate release from synaptosomal preparation of lesioned spinal cord obtained from animals implanted with the Step1 and a blank scaffold. Results are presented in FIG. 10-11. Step1 significantly decreases the spontaneous and K+-evoked glutamate release both at 24 hours and 8 days after lesion and implant, while is un-effective on GABA release.

Inflammation and Remyelination.

Figure 12:
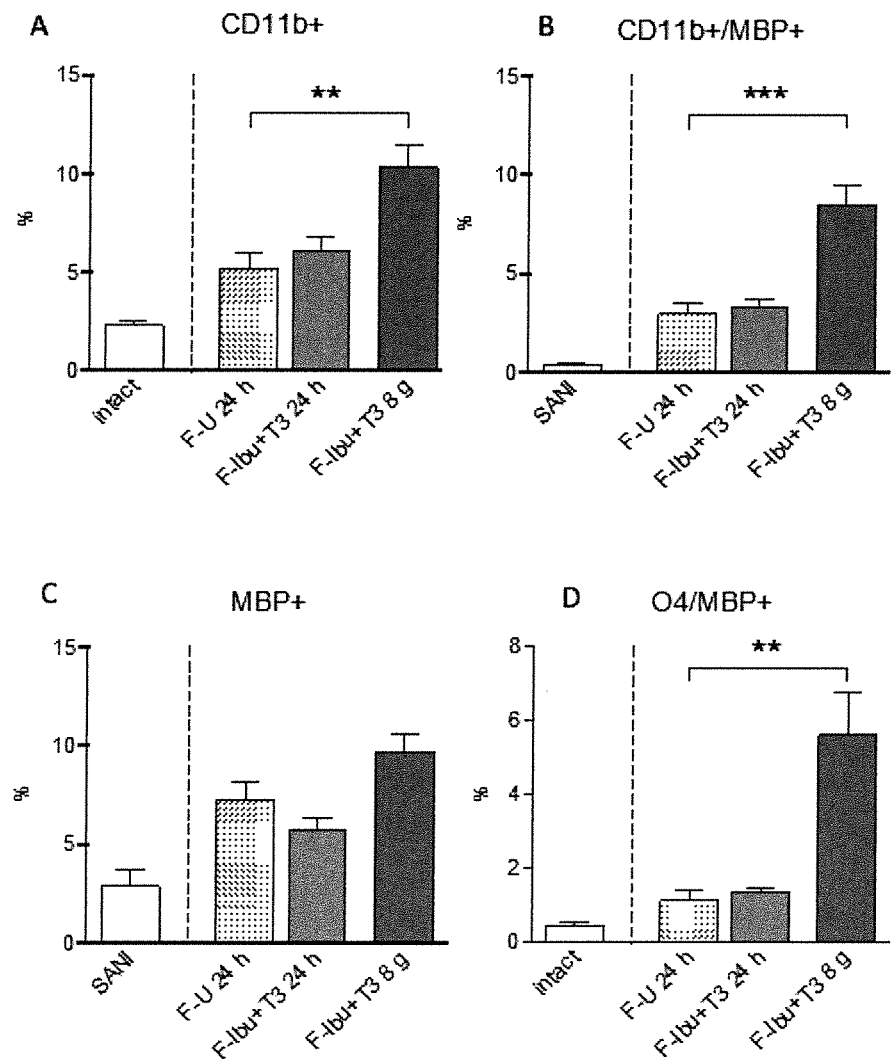
FIG. 12 shows the cell composition of the cellular infiltrate in the spinal cord of rat implanted with the invention, in comparison with the polymer, alone, proving the increase of fagocytes (CD11+) and promyelinating cells (MBP+).

In order to investigate if the scaffold with IBU and T3 affects inflammation and remyelination, we analysed the cell composition of lesioned spinal cord obtained from animals implanted with the scaffold with IBU and T3 and a blank scaffold. Results are presented in FIG. 12. We showed that the number of cells responsible for myelin debris removal (CD11b and CD11b/MBP-positive cells) increases in the spinal cord of animals implanted with Step1, such as the remyelinating cells (O4 and MBP positive). Moreover, we investigated expression regulation of genes encoding for inflammatory cytokines (FIG. 13), showing that Step 1 decreases the expression of key genes of the inflammation cascade (IL-1b and TNFa), also decreasing the expression level of the T3 inactivating enzyme D3.

The invention claimed is:

1. Electrospun polymeric fibers in the form of scaffold, wherein part or all of said fibers are loaded with the promyelinating agent 3,3,5-Triiodo-L-thyronine (T3) and another part or all of said fibers are loaded with an anti-inflammatory agent, for a local release of said promyelinating agent and said anti-inflammatory agent in a method of treating a spinal cord injury, wherein said electrospun polymeric fibers are suitable to be implanted directly on top of a lesion, wherein the local release of said promyelinating agent and said anti-inflammatory agent in a method of treating a spinal cord injury occurs over an estimated time of 8 to 14 days.

2. The electrospun fibers according to claim 1 wherein said anti-inflammatory agent is selected from a non-steroidal anti-inflammatory drug (NSAID), a salicylate, an anti-inflammatory glucocorticoid, and pirfenidone.

3. The electrospun fibers according to claim 2 wherein said anti-inflammatory agent is a non-steroidal anti-inflammatory drug (NSAID) selected from ibuprofen, flurbiprofen, diclofenac, and diclofenac with misoprostol, indomethacin, ketoprofen, fenbrufen, naproxen, sulindac, celecoxib, nabumetone, mefenamic acid, oxyphenbutazone, diflunisal, etodolac, fenoprofen, flurbiprofen, meclofenamate, meloxicam, nabumetone, oxaprozin, piroxicam, tolmetin, valdecoxib and propionic acid derivatives or their mixture.

4. The electrospun fibers according to claim 1 wherein said promyelinating agent is T3 and said anti-inflammatory agent is ibuprofen.

5. The electrospun fibers according to claim 1 wherein said polymeric fibers are biopolymeric fibers.

6. The electrospun fibers according to claim 1 wherein said polymer is selected from synthetic polyesters, polylactic acid (PLLA), polyglycolic acid (PGA), polycaprolactone (PCL) and/or their copolymers and/or their mixtures, polyurethanes, polyamides, fluorinate polymers, or their copolymers and/or mixture, or natural polymers selected from proteins, polysaccharides, polyesters, polypeptides and their copolymers and/or their mixtures.

7. The electrospun fibers according to claim 1 wherein said polymeric fibers are biocompatible fibers.

8. The electrospun fibers according to claim 1 wherein between 10 and 90% of said fibers are loaded with the promyelinating agent 3,3,5-Triiodo-L-thyronine (T3).

9. The electrospun fibers according to claim 1 wherein between 10 and 90% of said fibers are loaded with the anti-inflammatory agent.

10. The electrospun fibers according to claim 1 wherein all of said fibers are loaded with the promyelinating agent 3,3,5-Triiodo-L-thyronine (T3) and the anti-inflammatory agent.

11. The electrospun fibers according to claim 1 wherein the promyelinating agent and/or the anti-inflammatory agent is encapsulated within said fibers by non-covalent binding.

* * * * *